United States Patent [19]
Levenbook et al.

[11] Patent Number: 5,728,519
[45] Date of Patent: Mar. 17, 1998

[54] ASSAY FOR VIRULENT REVERTANTS OF ATTENUATED LIVE VACCINES AND KITS THEREFOR

[75] Inventors: Inessa S. Levenbook; Konstantin M. Chumakov, both of Bethesda; Laurie P. Norwood, Hyattsville, all of Md.; Igor Roninson, Chicago, Ill.

[73] Assignee: The United States of America as represented by the Department of Health and Human Services, Washington, D.C.

[21] Appl. No.: 361,337

[22] Filed: Dec. 21, 1994

Related U.S. Application Data

[63] Continuation-in-part of Ser. No. 246,373, May 18, 1994, which is a continuation of Ser. No. 607,742, Nov. 6, 1990, abandoned.

[51] Int. Cl.$^6$ ............................................. C12Q 1/68
[52] U.S. Cl. .................. 435/5; 424/130.1; 424/131.1; 424/184.1; 424/193.1; 424/199.1; 424/204.1; 424/205.1; 424/217.1; 424/93.1; 424/93.2; 424/520; 435/5; 435/6; 435/7.1; 435/91.1; 435/91.2; 435/91.5; 435/235.1; 435/236; 435/237; 435/239; 435/948; 436/501; 436/543; 436/547; 436/8; 436/811; 436/819; 536/23.1; 536/24.1; 536/24.3; 536/24.31; 536/24.32; 536/24.33; 935/77; 935/78
[58] Field of Search ........................ 424/130.1, 131.1, 424/184.1, 193.1, 199.1, 204.1, 205.1, 217.1, 93.1, 93.2, 520; 435/5, 6, 7.1, 91.1, 91.2, 91.5, 235.1, 236, 237, 239, 948; 436/501, 543, 547, 8, 811, 819; 536/23.1, 24.1, 24.3–24.33; 935/77, 78

[56] References Cited

PUBLICATIONS

Chumakov et al., "Assessment of the Viral RNA Sequence Heterogeneity for Control of OPV Neurovirulence," Brown, F., and Lewis, B.P. (eds): *Poliovirus Attenuation: Molecular Mechanisms and Practical Aspects*, Dev. Biol. Stand. Basel, Karger, vol. 78, pp. 79–89 (1993).

(List continued on next page.)

*Primary Examiner*—Ardin H. Marschel
*Attorney, Agent, or Firm*—Needle & Rosenberg, P.C.

[57] ABSTRACT

The present invention provides a method of classifying an unclassified live poliovirus vaccine as having an acceptable or unacceptable level of neurovirulence, comprising, prior to vaccine administration, the steps of: a) selectively amplifying a region of an unclassified poliovirus vaccine genome containing a nucleotide position predictive for increased neurovirulence using selectively mismatched primers, whereby a restriction endonuclease site in the selectively amplified region is created by introducing a site-specific mutation into the amplified region; b) digesting an amount of the amplified region with a restriction endonuclease that specifically cleaves the amplified sequences in revertant viruses which contain a reversion at the nucleotide position predictive for increased neurovirulence; c) digesting an amount of the amplified region with a restriction endonuclease that specifically cleaves the amplified sequences in nonrevertant viruses which contain the nucleotide position predictive for increased neurovirulence; d) quantifying the percentage of revertant viruses in the unclassified vaccine; and e) comparing the percentage of revertant viruses in the unclassified vaccine to the percentage of revertant viruses in an accepted reference vaccine, and unclassified vaccine with a highter percentage of revertant viruses than in the reference vaccine being classified as unacceptable or an unclassified vaccine with an equal or lower percentage of revertant viruses than in the reference vaccine being classified as acceptable. Related methods and kits are also provided.

17 Claims, 2 Drawing Sheets

OTHER PUBLICATIONS

Lu et al., "Quantitative Aspects of the Mutant Analysis by PCR and Restriction Enzyme Cleavage (MAPREC)," *PCR Methods and Applications* 3:176–180 (1993).

Ren et al., "Identification of Two Determinants that Attenuate Vaccine–Related Type 2 Poliovirus," *Journal of Virology* 65(3):1377–1382 (Mar., 1991).

Macadam et al., "The 5' Noncoding Regions of the Type 2 Poliovirus Vaccine Strain Contains Determinants of Attenuation and Temperature Sensitivity," *Virology* 181:451–458 (1991).

Christodoulou et al., "Mapping of Mutations Associated with Neurovirulence in Monkeys Infected with Sabin 1 Poliovirus Revertants Selected at High Temperature," *Journal of Virology* 64(10):4922–4929 (Oct., 1990).

Kawamura et al., "Determinants in the 5' Noncoding Region of Poliovirus Sabin 1 RNA that Influence the Attenuation Phenotype," *Journal of Virology* 63(3):1302–1309 (Mar., 1989).

Pollard et al., "Nucleotide Sequence of a Neurovirulent Variant of the Type 2 Oral Poliovirus Vaccine," *Journal of Virology* 63(11):4949–4951 (Nov., 1989).

Moss et al., "Mapping of Attenuating Sequences of an Avirulent Poliovirus Type 2 Strain," *Journal of Virology* 63(5):1884–1890 (May, 1989).

Westrop et a., "Genetic Basis of Attenuation of the Sabin Type 3 Oral Poliovirus Vaccine," *Virology* 63:1338–1344 (Mar., 1989).

J. W. Almond, "The Attenuation of Poliovirus Neurovirulence," *Ann. Rev. Microbiol* 41:153–80 (1987).

Evans et al., "Increased neurovirulence associated with a single nucleotide change in a noncoding region of the Sabin type 3 poliovaccine genome," *Nature* 314(11):548–550 (Apr., 1985).

Fig. 1

Histological Lesion Score vs. Total content of 480-A + 525-C revertants, %

○ Vaccine Lots
▲ Experimental Lots
□ Reference

ASSAY FOR VIRULENT REVERTANTS OF ATTENUATED LIVE VACCINES AND KITS THEREFOR

BACKGROUND OF THE INVENTION

This application is a continuation-in-part of U.S. Ser. No. 08/246,373, filed May 18, 1994, which is a continuation of U.S. Ser. No. 07/607,742 filed Nov. 6, 1990, abandoned.

FIELD OF INVENTION

The present invention provides a method of assaying live attenuated viral vaccine lots for acceptable or unacceptable levels of reversion to virulence. The method utilizes detection and quantitation of reversion of certain mutations in the genome of the virus, and the association of various levels of the revertants with virulence, and thus avoids the use of animals required by previous tests.

BACKGROUND ART

The currently used live poliomyelitis vaccine developed by Sabin (Sabin, Ann. N.Y. Acad. Sci. 61:924–938 (1955); Sabin, PASB Sc. Pub. 44:14–33 (1959); Sabin, J. Am. Med. Assoc. 194:130–134 (1965)) comprises three attenuated viral strains, corresponding to poliovirus type 1, type 2 and type 3. Genomic variability within RNA virus populations is a consequence of the high error rate inherent in the replication of RNA genomes (Holland et al., Science 215:1576–1585 (1982); Ward and Flanegan., Journal of Virology 62:558–562 (1988); de LaTorre et al., Journal of Virology 64:664–671 (1990)), and has led to the introduction of quasispecies concept to virology (Domingo et al., Gene 40:1–8 (1986)). Studies of poliovirus replication have indicated an error frequency of $10^{-3}$ to $10^{-4}$ per nucleotide incorporated into nascent poliovirus RNA (de La Torre et al., 1990; Ward and Flanegan, Journal of Virology 66:3784–3793 (1992)). Because the poliovirus genome consists of ca. 7400 nucleotides, this error rate suggests that most newly synthesized poliovirus RNA molecules differ in at least one nucleotide from the sequence of the parental template RNA. Consequently, every stock of poliovirus represents a population of vital genomic sequences, which compete with each other for dominance in the mixed population of sequences. The sequence population is therefore dynamic, with the relative abundance of each sequence, at any one time, reflecting the parental virus stock and the relative efficiency of the sequence under the vital growth conditions utilized. Any alteration in vital growth conditions can affect this population distribution by altering the relative replication efficiency of the competing vital sequences.

The concept of a dynamic viral population has direct implications for live viral vaccines and provides an explanation for rapid changes of viral phenotype that can occur during manufacture or after administration to vaccines. Oral poliovirus vaccine (OPV) produced with Sabin strains has had a major role over the past 30 years in eradicating poliomyelitis in developed countries. The attenuated Sabin strains were derived from wild-type isolates by rapid in vitro passaging at low temperatures followed by plaque purification. They possess several genetic markers which are believed to be associated with attenuation, e.g. $rct_{40}$ (reduced, relative to wild type, replicatire capacity at elevated temperatures) and low neurovirulence upon inoculation into the central nervous system of monkeys (Sabin, N.Y. Acad. Sci. V:113–127 (1957a); Sabin, Perspectives in Virology 2:90–108, M. Pollard, ed., Burgess Publishing Company, Minneapolis, Minn. (1961)). Changes in the $rct_{40}$ or monkey neurovirulence phenotypes can occur following in vitro or in vivo passage of the Sabin strains (Benyesh-Melnick and Melnick, So. Pub. No. 44:179–198, Pan-American Health Organization, Washington, P.A.H.O. (1959); Sabin, J.A.M.A. 164:1216–1223 (1957b); Sabin, 1961). OPV production, therefore, requires strict monitoring of the production process and requires testing of the final lots to ensure consistency of vaccine manufacture (World Health Organization, WHO Tech. Rep. Ser. 800:30–65 (1990)). The standard test which has been used for neurovirulence testing of vaccine lots is performed by intrathalmic and/or intraspinal inoculation of monkeys with each manufactured vaccine lot, with subsequent pathological evaluation of developing lesions. This test is very expensive, slow and its results may vary since individuals responses of monkeys to the inoculum may differ significantly. The same problems are shared by animal safety tests used for other live attenuated vaccines.

The high mutation rate inherent in poliovirus RNA replication results in the presence of a variety of nascent mutations in every virus preparation. These mutations are randomly distributed along the vital genome (Ward and Flanegan, 1992) and do not accumulate beyond the limits of detection unless they provide some replicative advantage to the virus. Therefore microevolution of the viral population proceeds by occurrence of random mutations and competition of numerous viral variants resulting in accumulation of those variants that provide replicative advantages under particular growth conditions. Recently some of the molecular changes occurring in Sabin strains after administration to vaccinees and associated with partial deattenuation were identified (Evans et al., Nature 314:548–550 (1985); Westrop et al., Journal of Virology 63:1338–1344 (1989); Kawamura et al., Journal of Virology 63:1302–1309 (1989); Christodoulou et al., Journal of Virology 64:4922–4929 (1990); Pollard et al., Journal of Virology 63:4949–4951 (1989); Macadam et al., Virology 181:451–458 (1991a)).

Specifically, studies of poliovirus attenuation determinants have identified several point mutations that affect neurovirulence of serotypes 1 and 2 of poliovirus (Christodoulou, et al., 1990; Kawamura et al., 1989; Macadam et al., 1991a; Moss et al., Journal of Virology 63:1884–1890 (1989); Ren et al., Journal of Virology 65:1377–1382 (1991)) and serotype 3 (Almond, Ann. Rev. Microbiol. 41:153–180 (1987)). However, as provided by the present invention, surprisingly, not all reversions of point mutations are associated with reversion to neurovirulence.

Sequence changes in poliovirus RNA have been previously analyzed by direct sequencing of viral RNA (Evans et al., 1985; Weeks-Levy et al., Vaccines 88:223–227, Cold Spring Harbor Laboratory Press, Cold Spring Harbor, N.Y. (1988)), a method which is not particularly sensitive for detection of sequence variants present at low abundance. For example, this approach failed to reveal mutants at position 472 in type 3 poliovirus vaccine lots (Weeks-Levy et al., 1988).

Because low neurovirulence in monkeys is a key marker of viral attenuation, it is important to ensure that neurovirulent revertants do not accumulate during vaccine production. Thus, there is a great need to develop alternative tests for the stability of attenuated vaccine microorganisms that avoid the expensive and slow primate testing. The present invention fills this need by providing assays to determine reversion of vaccine lots to neurovirulence by quantitating the presence of specific revertant poliovirus in vaccine lots and correlating that amount with acceptable or unacceptable levels of revertant poliovirus in the lot. Specific assays are provided for each of type 1, 2 and 3 oral poliovirus vaccine (OPV).

SUMMARY OF THE INVENTION

The present invention provides a method of classifying an unclassified live poliovirus vaccine as having an acceptable or unacceptable level of neurovirulence, comprising, prior to vaccine administration, the steps of: a) selectively amplifying a region of an unclassified poliovirus vaccine genome containing a nucleotide position predictive for increased neurovirulence using selectively mismatched primers, whereby a restriction endonuclease site in the selectively amplified region is created by introducing a site-specific mutation into the amplified region; b) digesting an amount of the amplified region with a restriction endonuclease that specifically cleaves the amplified sequences in revertant viruses which contain a reversion at the nucleotide position predictive for increased neurovirulence; c) digesting an amount of the amplified region with a restriction endonuclease that specifically cleaves the amplified sequences in nonrevertant viruses which contain the nucleotide position predictive for increased neurovirulence; d) quantifying the percentage of revertant viruses in the unclassified vaccine; and e) comparing the percentage of revertant viruses in the unclassified vaccine to the percentage of revertant viruses in an accepted reference vaccine, an unclassified vaccine with a higher percentage of revertant viruses than in the reference vaccine being classified as unacceptable or an unclassified vaccine with an equal or lower percentage of revertant viruses than in the reference vaccine being classified as acceptable.

Also provided is a method for classifying an unclassified live poliovirus vaccine as having an acceptable or unacceptable level of neurovirulence, comprising the steps of: a) quantifying the percentage of revertant viruses contained in the unclassified vaccine prior to administration by testing for the presence of a reversion at a nucleotide position predictive for increased neurovirulence; and b) comparing the percentage of revertant viruses in the unclassified vaccine to the percentage of revertant viruses in an accepted reference vaccine, an unclassified vaccine having a higher percentage of the reversion predictive for increased neurovirulence than in the reference vaccine being classified as unacceptable or an unclassified vaccine with an equal or lower percentage of the reversion predictive for increased neurovirulence than in the reference vaccine being classified as acceptable.

Also provided in the present invention is a method for determining the suitability of a cell culture for poliovirus vaccine production, comprising the steps of: a) culturing an attenuated live poliovirus strain having a nucleotide position predictive for increased neurovirulence in a selected cell culture; b) quantifying the percentage of revertant viruses having a reversion at a position predictive for increased neurovirulence; and c) comparing the percentage of revertant viruses having the reversion predictive for increased neurovirulence to the percentage of revertant viruses in an accepted reference poliovirus strain, the presence of a greater percentage of reversions at the position predictive for increased neurovirulence in the poliovirus strain cultured in the selected cell culture than in the reference poliovirus strain indicating a cell culture unsuitable for poliovirus vaccine production.

In addition, the present invention provides a method for determining the suitability of an attenuated poliovirus strain or seed poliovirus lot for vaccine production, comprising the steps of: a) culturing an attenuated live poliovirus strain or seed poliovirus lot in a selected cell culture; b) quantifying the percentage of revertant viruses having a reversion at a position predictive for increased neurovirulence; and c) comparing the percentage of revertant viruses having the reversion predictive for increased neurovirulence to the percentage of revertant viruses in an accepted reference poliovirus strain, the presence of a greater percentage of reversions at the position predictive for increased virulence in the poliovirus strain or seed poliovirus lot cultured in the selected cell culture than in the accepted reference poliovirus strain indicating a poliovirus strain or seed poliovirus lot unsuitable for poliovirus vaccine production.

Also provided is a kit for classifying a poliovirus type 2 vaccine as having either an acceptable or unacceptable level of monkey neurovirulence, comprising: a) a first and second oligonucleotide which selectively binds to the poliovirus type 2 RNA or corresponding DNA so as to detectably amplify by polymerase chain reaction the region containing position 481 of the viral genome; and b) a reagent for quantification of an A to G reversion at position 481 in the amplified region, wherein each oligonucleotide and the reagent are contained in separate containers.

Additionally, a kit for classifying a poliovirus type 1 vaccine as having either an acceptable or unacceptable level of monkey neurovirulence is provided, comprising: a) a first and second oligonucleotide which selectively binds to the poliovirus type 1 RNA or corresponding DNA so as to delectably amplify by polymerase chain reaction the region containing position 480 of the viral genome; and b) a reagent for quantification of a G to A reversion at position 480 in the amplified region, wherein each oligonucleotide and the reagent are contained in separate containers.

Further provided in the present invention is a kit for classifying a poliovirus type 1 vaccine as having either an acceptable or unacceptable level of monkey neurovirulence, comprising: a) a first and second oligonucleotide which selectively binds to the poliovirus type 1 RNA or corresponding DNA so as to detectably amplify by polymerase chain reaction the region containing position 525 of the vital genome; and b) a reagent for quantification of a U to C reversion at position 525 in the amplified region, wherein each oligonucleotide and the reagent are contained in separate containers.

The present invention also provides a method of determining the acceptability of an unclassified vaccine, comprising the steps of: a) introducing a site specific mutation into a DNA sequence, of the unclassified vaccine, amplified by the polymerase chain reaction by using selectively mismatched primers; b) digesting the DNA sequence with a restriction endonuclease that specifically cleaves DNA sequences containing a reversion; c) quantifying the percentage of revertants in the unclassified vaccine; and d) comparing the percentage of revertant viruses in the unclassified vaccine to the percentage of revertant viruses in an accepted reference vaccine, an unclassified vaccine having a higher percentage of reversion than in the accepted reference vaccine being classified as unacceptable and an unclassified vaccine with an equal or lower percentage of reversion than in the accepted reference vaccine being classified as acceptable.

BRIEF DESCRIPTION OF THE DRAWINGS

FIG. 1 shows the correlation between the content of 480-A and 525-C in type 1 OPV and experimental samples of Sabin 1, and the mean lesion scores (MLS) obtained in the MNVT (triangles). Results for commercial vaccine lots (open circles) and the U.S. neurovirulence reference (open squares) are shown for comparison.

DETAILED DESCRIPTION OF THE INVENTION

Figure 2:
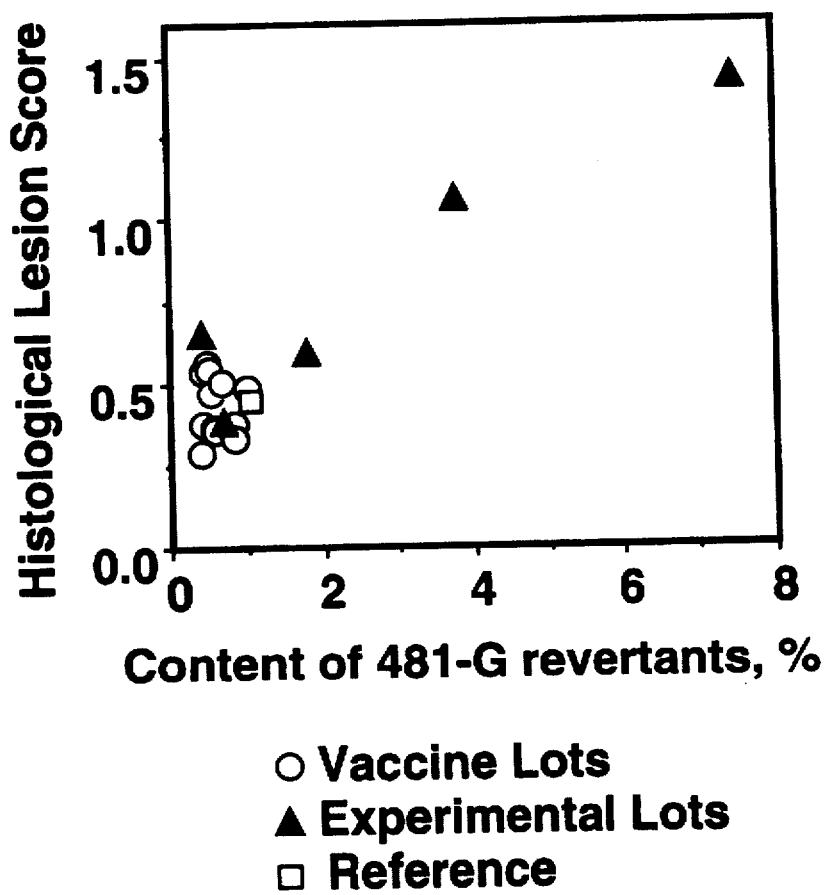
FIG. 2 shows the correlation between the content of 481-G revertants in type 2 OPV and the MLS obtained in the MNVT (closed squares). Results for commercial monopools (open circles) and the U.S. neurovirulence reference (triangles) are shown for comparison.

The present invention is more particularly described in the following examples and figures which are intended as illustrative only since numerous modifications and variations therein will be apparent to those skilled in the art.

The present invention provides a method of classifying an unclassified live poliovirus vaccine as having an acceptable or unacceptable level of neurovirulence, comprising, prior to vaccine administration, the steps of:

a) selectively amplifying a region of an unclassified poliovirus vaccine genome containing a nucleotide position predictive for increased neurovirulence using selectively mismatched primers, whereby a restriction endonuclease site in the selectively amplified region is created by introducing a site-specific mutation into the amplified region;

b) digesting an amount of the amplified region with a restriction endonuclease that specifically cleaves the amplified sequences in revertant viruses which contain a reversion at the nucleotide position predictive for increased neurovirulence;

c) digesting an amount of the amplified region with a restriction endonuclease that specifically cleaves the amplified sequences in nonrevertant viruses which contain the nucleotide position predictive for increased neurovirulence;

d) quantifying the percentage of revertant viruses in the unclassified vaccine; and e) comparing the percentage of revertant viruses in the unclassified vaccine to the percentage of revertant viruses in an accepted reference vaccine, an unclassified vaccine with a higher percentage of revertant viruses than in the reference vaccine being classified as unacceptable or an unclassified vaccine with an equal or lower percentage of revertant viruses than in the reference vaccine being classified as acceptable.

As used in the specification and in the claims, "a" can mean one or more, depending upon the context in which it is used.

The term "revertant" refers to a microorganism with increased virulence including the restoration of the original nucleotide sequence present in the original pathogenic strain or by the novel mutation in the genome of a vaccine microorganism leading to increased virulence.

The present invention has use in the detection of revertants of various types of microorganisms. Initial work has been performed on the poliovirus. However, the present invention has possible use with other types of viruses which are used to make vaccines, particularly those viruses which are prone to reversion. Other possible types of vaccine viruses are attenuated strains of mumps, measles, rubella, varicella, Dengue, Venezuelan equine encephalitis, eastern equine encephalitis, vaccinia, rotaviruses, influenza viruses, etc. The present invention can also be used to detect revertants or mutants in rickettsial (Strain E) and bacterial vaccines such as, for example, BCG, live vaccine against plague, tularemia, brucellosis, anthrax, typhoid fever and shigellosis vaccines.

As used herein, "type 1, 2 and 3," "serotype 1, 2 and 3" and "Sabin type 1, 2 and 3" etc. are interchangeable terms for the polioviruses.

By "selectively amplifying" is meant that primarily only the target region, rather than background, is amplified.

A nucleotide position predictive for increased neurovirulence includes one or more nucleotide position(s) in the viral genome found to correlate with reversion of an attenuated virus to neurovirulence and particularly a specific nucleotide at that position(s) for which elevated levels of viruses containing the nucleotide are present in and associated with a vaccine that has revered to neurovirulence. In this application the term "marker" is used interchangeably with "nucleotide position predictive for increased neurovirulence." Thus as used in the present application, these two terms refer to a difference or differences between the nucleotide sequence of a virulent form of a microorganism, particularly a virus, and the nucleotide sequence of a corresponding attenuated microorganism used in the vaccine. The marker can be a single difference (one point difference) in a nucleotide sequence or differences in more than one nucleotide.

For example, in Sabin type 1, neurovirulent revertants can have a G to A substitution at nucleotide position 480 ("480-A"). Another example in Sabin type 1 of a neurovirulent revertant is a virus having a U to C substitution at nucleotide position 525 ("525-C"). Either of these markers can be present at levels high enough to render the vaccine unacceptable. However, if one marker is present at acceptable levels, the level of the other type 1 marker should be quantitated and must also be present in acceptable levels for the vaccine to be acceptable. By way of another example, in type 2, a nucleotide position predictive of increased neurovirulence is position 481, wherein revertant neurovirulent viruses contain an A to G substitution ("481-G"). As yet another example, in type 3, a nucleotide position predictive of increased neurovirulence is position 472, wherein revertant neurovirulent viruses have a U to C substitution ("472-C"). As exemplified below, the presence of reversion of any one of these point mutations from the original sequence of the attenuated virus at levels greater than those found in an accepted reference vaccine indicates an unacceptable level of neurovirulence in the vaccine. The presence of reversion of one of these point mutations in a vaccine in equal or lower amounts than that found in an accepted reference vaccine indicates a vaccine with an acceptable level of neurovirulence.

An accepted reference vaccine for any assay herein can typically be a vaccine that has passed the standard monkey neurovirulence test (MNVT). In an accepted reference vaccine, the percentage of viruses which contain a selected point mutation, e.g., 481-G, 525-C, 480-A, 472-C, can readily be determined as taught herein. The levels of the same point mutation are measured in both the reference vaccine and in the unclassified vaccine being assayed for classification.

The present invention additionally provides a method for classifying an unclassified live poliovirus vaccine as having an acceptable or unacceptable level of neurovirulence, comprising the steps of:

a. quantifying the percentage of revertant viruses contained in the unclassified vaccine prior to administration by testing for the presence of a reversion at a nucleotide position predictive for increased neurovirulence; and b. comparing the percentage of revertant viruses in the unclassified vaccine to the percentage of revertant viruses in an accepted reference vaccine, an unclassified vaccine having a higher percentage of the reversion predictive for increased neurovirulence than in the reference vaccine being classified as unacceptable or an unclassified vaccine with an equal or lower percentage of the reversion predictive for increased neurovirulence than in the reference vaccine being classified as acceptable.

Further, the present invention provides a method for determining the suitability of a cell culture for poliovirus vaccine production, comprising the steps of:

c. culturing an attenuated live poliovirus strain having a nucleotide position predictive for increased neurovirulence in a selected cell culture;

d. quantifying the percentage of revertant viruses having a reversion at a position predictive for increased neurovirulence; and e. comparing the percentage of revertant viruses having the reversion predictive for increased neurovirulence to the percentage of revertant viruses in an accepted reference poliovirus strain, the presence of a greater percentage of reversions at the position predictive for increased neurovirulence in the poliovirus strain cultured in the selected cell culture than in the reference poliovirus strain indicating a cell culture unsuitable for poliovirus vaccine production.

The present invention also provides a method for determining the suitability of an attenuated poliovirus strain or seed poliovirus lot for vaccine production, comprising the steps of:

f. culturing an attenuated live poliovirus strain or seed poliovirus lot in a selected cell culture;

g. quantifying the percentage of revertant viruses having a reversion at a position predictive for increased neurovirulence;

h. comparing the percentage of revertant viruses having the reversion predictive for increased neurovirulence to the percentage of revertant viruses in an accepted reference poliovirus strain, the presence of a greater percentage of reversions at the position predictive for increased virulence in the poliovirus strain or seed poliovirus lot cultured in the selected cell culture than in the accepted reference poliovirus strain indicating poliovirus strain or seed poliovirus lot unsuitable for poliovirus vaccine production.

Also provided is a method of determining the acceptability of an unclassified vaccine, comprising the steps of:

a. introducing a site specific mutation into a DNA sequence, of the unclassified vaccine, amplified by the polymerase chain reaction by using selectively mismatched primers;

b. digesting the DNA sequence with a restriction endonuclease that specifically cleaves DNA sequences containing a reversion;

c. quantifying the percentage of revertants in the unclassified vaccine; and d. comparing the percentage of revertant viruses in the unclassified vaccine to the percentage of revertant viruses in an accepted reference vaccine, an unclassified vaccine having a higher percentage of reversion than in the accepted reference vaccine being classified as unacceptable and an unclassified vaccine with an equal or lower percentage of reversion than in the accepted reference vaccine being classified as acceptable.

Various types of tests can be used to quantify the amount or percentage of revertant microorganisms. Polymerase chain reaction (PCR) amplification and restriction enzyme digestion are preferably used to quantify revertants. However, other tests, such as hybridization with specific oligonucleotides, RNAse protection, chemical cleavage assays or assays based on ligation of specific oligonucleotides can also be used to test for the presence of the specific predictive nucleotide (marker). However, any assay requires the quantification of the reversion to determine the acceptability of the vaccine, etc.

When PCR technology is used to assay the revertants, various procedures can be used to label the amplified sequence. For example, the anti-sense primer can be lableled with $^{32}P$, the sense primer can be labeled with $^{32}P$ or one of the nucleotides in the nucleotide mix which is used to create the amplified sequences can be labeled. Non-radioactive labeling such as enzyme-based assays, chemiluminescence, and fluorescence energy transfer can also be used, as well as sensitive methods for detection of unlabeled DNA. Separation and quantitation of DNA fragments can be achieved by any of several methods including gel electrophoresis. For example, DNA fragments produced by restriction enzyme cleavage fragments can be separated and quantitated by high performance liquid chromatography (HPLC).

The oligonucleotides used as primers should contain enough nucleotides so that they specifically bind only to the desired nucleotide sequence, usually at least about 8 nucleotides, preferably 10 to 50 nucleotides, more preferably 15 to 40 nucleotides. The oligonucleotides should bind to regions in close proximity to the nucleotide position predictive for increased neurovirulence under investigation. The region amplified by PCR technology will usually have a length of about 60 to 600 nucleotides.

Amplification of the marker-containing region by PCR is convenient since it allows one to use very small amounts of RNA or DNA from the vaccine microorganism for the test. It may be possible, however, to detect and measure the marker directly using the genomic DNA, RNA or cDNA synthesized from genomic RNA of the vaccine microorganism, without amplifying the marker-containing region by PCR or any other technique.

The preferred procedure for detection of the marker associated with reversion to virulence consists of digestion of the marker-containing DNA segment with a restriction enzyme which cuts the DNA only if the marker sequence is present, followed by measuring the proportion of DNA digested with the above restriction enzyme. The marker-specific restriction site may pre-exist in the DNA sequence of the revertant, or it may be created by modifying the sequence of cDNA or of the PCR-amplified segment by making appropriate changes in at least one oligonucleotide used for cDNA synthesis or for PCR. Alternatively, the reversion marker may be detected by the absence rather than by the presence of a restriction site. The marker can also be detected and measured by hybridization with marker-containing oligonucleotide probes corresponding either to the vaccine-specific or to the revertant-specific sequences, followed by comparison of the hybridization signal obtained with each of the probes. It is also possible to carry out PCR amplification using two pairs of oligonucleotides, one selected so as to selectively amplify the vaccine sequence and the other selected to amplify the revertant sequence; the yields of the two PCR reactions can then be compared to each other to determine the incidence of the revertant. Furthermore, the same markers can also be detected and measured by denaturation of double-stranded DNA, RNA or cDNA of the vaccine microorganism, followed by reassociation and detection of mismatched duplexes by cleavage with enzymes or chemical reagents that specifically recognize mismatched DNA or RNA duplexes, with subsequent measurement of the cleavage products. Detection of the marker associated with reversion to virulence can also be by detection of an electrophoretic mobility shift in gels with gradients of denaturing agents.

The present invention additionally provides kits for determining whether any specific virus type vaccine has an acceptable or unacceptable level of neurovirulence. Specifically, the invention provides a kit for classifying a poliovirus type 2 vaccine as having either an acceptable or unacceptable level of monkey neurovirulence, comprising:

a. a first and second oligonucleotide which selectively binds to the poliovirus type 2 RNA or corresponding DNA so as to detectably amplify by polymerase chain reaction the region containing position 481 of the viral genome; and b. a reagent for quantification of an A to G reversion at position 481 in the amplified region, wherein each oligonucleotide and the reagent are contained in separate containers.

Also provided is a kit for classifying a poliovirus type 1 vaccine as having either an acceptable or unacceptable level of monkey neurovirulence, comprising:

a. a first and second oligonucleotide which selectively binds to the poliovirus type 1 RNA or corresponding DNA so as to detectably amplify by polymerase chain reaction the region containing position 525 of the viral genome; and b. a reagent for quantification of a U to C reversion at position 525 in the amplified region, wherein each oligonucleotide and the reagent are contained in separate containers.

Additionally provided is a kit for classifying a poliovirus type 1 vaccine as having either an acceptable or unacceptable level of monkey neurovirulence, comprising:

a. a first and second oligonucleotide which selectively binds to the poliovirus type 1 RNA or corresponding DNA so as to detectably amplify by polymerase chain reaction the region containing position 525 of the viral genome; and b. a reagent for quantification of a U to C reversion at position 525 in the amplified region, wherein each oligonucleotide and the reagent are contained in separate containers.

Oligonucleotides for any kit can be selected by standard means, given the teaching herein, and several examples of oligonucleotides are provided herein. A useful oligonucleotide is one that selectively binds to the target nucleic acid so that the target region is amplified; therefore, oligonucleotides that randomly bind or that bind to regions other than regions that will produce amplified target region are excluded from this kit. Reagents can be selected as taught and exemplified herein for quantifying any specific nucleotide substitution.

STATEMENT CONCERNING UTILITY

The present invention has many utilities which are apparent. The present invention provides a convenient, rapid, less expensive, and more sensitive means of assaying poliovirus vaccines for acceptable or unacceptable levels of neurovirulence than previous methods. All commercial vaccine monopools possess some level of revertants, and it is known that, therefore, individual lots must be tested. The present method provides a means to assay vaccine lots for neurovirulence without sacrificing mammals, since measurement with the present method correlates with measurement by MNVT.

Additionally, the present method allows for determining whether specific cell types are suitable or unsuitable for production of virus, since it teaches that percentages of virulent revertants can vary with the cell type in which the vaccine is produced.

The present assay can be applied to quantitate any mutation associated with reversion of any vaccine, and further, it can be applied to determine whether elevated levels of any particular mutation in a vaccine lot are associated with reversion to neurovirulence and to determine what amount of individual revertant genotypes in a vaccine lot is acceptable and unacceptable for vaccine use.

EXAMPLES

Two point mutations were shown to be major determinants of attenuation of type 3 OPV (Evans et al., 1985; Westrop et al., 1989). The first mutation, a C to U transition at position 472 in the F-domain of the 5'-untranslated region, reduces the template activity of the viral RNA in protein synthesis (Svitkin et al., Virology 147:243–252 (1985); Svitkin et al., Virology 166:394–404 (1988); Svitkin et al., Virology 175:103–109 (1990)). The second mutation, at position 2034, changes phenylalanine to serene in VP3, causing a virion assembly defect and making viral replication temperature-sensitive (Macadam et al., 1991 a; Macadam et al., Journal of Virology 65:5225–5231 (1991b)). By using sensitive MAPREC, it has been shown that revertants with C at position 472 rapidly accumulate during virus propagation in vitro, while position 2034 remains stable. The abundance of revertants at position 472 correlates quantitatively with neurovirulence in monkeys and is predictive of the MNVT results.

Mutants consistently accumulating in Sabin I poliovirus during serial passaging in vitro were identified by sequence heterogeneity assay (SHA) and quantitated using mutant analysis by PCR and restriction enzyme cleavage (MAPREC). Only four unstable genomic sites were identified in virus passaged 10 times in African green monkey kidney (AGMK) cells, and eight sites in virus passages in Vero cells. Mutations accumulated both in untranslated regions of RNA (nucleotides 480, 525 and 7441) and in coding sequences, as missense (nucleotides 1449, 4944, and 6203) or silent (nucleotides 1123 and 1141) mutations. The most prominent selectable mutations were found at complementary nucleotides 480 and 525 of the 5'-untranslated region (5'-UTR) of the Sabin strain, changing the G:U pair in F-domain to either A:U or G:C variants. These two variants are shown herein to have an increased neurovirulence in monkeys. The G:C variant accumulated during passage in Vero cells, while A:U variant accumulated in CV-1 cells. Monopools of type 1 oral poliovirus vaccine (OPV) made by seven manufacturers were found to contain both 480-A and 525-C revertants at a combined level of 1.1–2.7%. Viral samples with increased amounts of these revertants had higher neurovirulence in monkeys. Thus quantitation of these reversions by MAPREC can be prognostic for results of the MNVT and can be used for monitoring type 1 OPV consistency.

Mutations that consistently accumulated in attenuated Sabin 2 strain of poliovirus during propagation in cell cultures were identified by SHA and quantified by MAPREC. Eight additional sites previously identified in stool isolates were also examined by MAPREC in the virus passages. The pattern of selectable mutations and the rate of their accumulation depended on the type and confluence of the cell culture and the temperature of virus growth. Five unstable genomic sites were identified in Sabin 2 virus passaged ten times at 34° C. in AGMK cells, with the mutations accumulating in the range from 1 to 24%. Accumulation of these mutations did not appear to result in a loss of attenuated phenotype, since the virus passaged at these conditions passed the MNVT. The content of 481-G revertant known to be related to neurovirulence in monkeys did not increase. Thus, upon growth of Sabin 2 virus in AGMK cells at 34° C., key determinant(s) of attenuation remained stable, and the mutations that occurred did not affect monkey neurovirulence. In virus passaged ten times at 37° C. in AGMK cells four unstable genomic sites were identified, in some of them accumulating up to 12% of mutants, and this virus sample severely failed the MNVT. Virus passaged in Vero cells at 34° C. and 37° C. accumulated mutants at seven and 14 genomic sites, respectively, including 481-G in both cases, with almost complete substitution of the original nucleotides at some of the sites 44 commercial monopools of type 2 OPV were tested, and all of them contained 481-G revertants in the range of 0.4–1.1%. An increase of the 481-G revertants in passaged viruses to the level 4% and above correlated with failure of these samples in the MNVT. Therefore, quantitation of 481-G revertants by MAPREC predicted results of MNVT and can be used to monitor acceptability of type 2 OPV lots. Since the pattern of selectable mutations differed in viruses grown in the two cell cultures used in this study, specific mutation profiles can be determined for each cell substrate used for vaccine production to assess manufacturing consistency.

The present invention demonstrates that U to C reversion at position 472 of Sabin type 3, G to A reversion at position 480 of Sabin type 1, A to G reversion at position 481 of Sabin type 2, and U to C reversion at position 525 of Sabin type 1, accumulate during virus passaging in vitro. These reversions all occur in the F-domain of the poliovirus 5'-untranslated region, as shown herein for all three Sabin serotypes. The present invention demonstrates a correlation between detection of elevated levels of these reversions and neurovirulence as measured by the monkey neurovirulence assay. Therefore, these reversions are predictive of increased neurovirulence. The direct molecular assay of the OPV genetic stability described herein can be used for the improvement of vaccine manufacturing consistency and evaluation of the genetic stability of prospective vaccine strains and see virus lots.

Cell culture and viruses

Continuous cultures of Vero cells (from ATCC, used at passage levels 144–150) were maintained in MEM with 2 mM glutamine and 10% fetal bovine serum. Primary cultures of AGMK cells (BioWhittaker, Gaithersburg, Md.) were used upon receipt without reculturing. Cultures were infected at 95% confluence with the Sabin strain of poliovirus type 1, 2 or 3 (SO+3 passage level) at a multiplicity of infection of about 1–2 TCID$_{50}$ per cell and incubated at 34° C. or 37° C. in medium without serum. In some experiments, cultures of Vero cells were infected three days after reaching confluence. After complete cytopathic effect in 2–5 days following infection, cultures were frozen and used for further passage and to extract RNA for molecular analysis by SHA and MAPREC. Ten consecutive virus passages were made in Vero and AGMK cells at each temperature.

RNA and cDNA preparation, SHA, and MAPREC

To identify those mutations that consistently accumulated in the viral population upon passaging, virus samples were first analyzed after ten passages in cell culture, allowing selectable mutations to accumulate to detectable levels. Viral RNA was isolated by phenol/SDS extraction and cDNA prepared by reverse transcription with Mo-MuLV reverse transcriptase and random hexanucleotide or other primers where indicated (Chumakov et al., Proc. Natl. Acad. Sci. USA 88:199–203 (1991); Chumakov et al., Journal of Virology 66:966–970 (1992a); Lu at al., PCR Methods Appl. 3:176–180 (1993)).

MAPREC was performed with some modifications (Lu et al., 1993). Briefly, PCR was done with unlabeled primers, one of which was taken in 10-fold excess to ensure asymmetric amplification and accumulation of single-stranded DNA. DNA was labeled during second-strand synthesis by DNA-polymerase primer extension reaction with $^{32}P$-labeled primer. Samples of labeled DNA were treated with respective restriction enzymes; digestion products were separated by electrophoresis in polyacrylamide gel and visualized and quantitated in a Betascope B603 blot analyzer (Betagen).

Sequence heterogeneity assay

SHA was performed by cycle-sequencing of PCR-amplified fragments of high passages of Sabin 1 or 2 strain. For type 1, 11 overlapping 800-base pair DNA segments were synthesized by PCR on cDNA template and purified by precipitation with 50% isopropanol at room temperature (10 min). For type 2, 13 overlapping DNA segments spanning the entire type 2 poliovirus genome were used. Each segment was sequenced using dsDNA cycle-sequencing kit (Gibco BRL) and three primers. Electrophoresis was performed in 30×40-cm polyacrylamide gel plates with 0.4- to 1.2-mm wedge spacers. Overexposed autoradiographs were carefully inspected for the presence of minor bands indicating possible sequence heterogeneity. Homogenous cDNA plasmid pVS(1)IC-0(T) (Kohara et al., Virology 151:21–30 (1986) containing a copy of the entire Sabin 1 genome was used as a homogenous control for type 1. This screening method proved to be very sensitive, in some cases detecting sequence heterogeneity below the level of 1%.

Analysis of the 5'-end

PCR amplification of the 5' end was performed in the presence of a "template extension molecule" (TEM), a synthetic oligonucleotide. For Sabin type 1 and 2, AGCTGATCGA TGGGCTACCA TGCGTACCCT AGCTGTTAAA ACAGCTCTGG GGTTGGACTC ACCCCAGAGG AAA (listed herein as SEQ ID NO:1) was used as TEM. This TEM has a 3' end complementary to the cDNA and a 35-bp DNA stretch used as a template for extension of cDNA to create a binding site for a PCR amplification primer. Underlined nucleotides are those which do not correspond to the viral RNA sequence. Nucleotides 1–30 create a site for binding of the sense PCR primer; the terminal three adenosines block use of TEM as a primer to copy cDNA sequences, and mismatches at positions 21, 24, and 26 of the viral genome create a Hinfl site, which was used to confirm that PCR-amplified DNA was generated on the cDNA template and is not a copy of the TEM. After PCR amplification with the primers AGCTGATCGA TGGGCTACCA TGCGTACCCT (sense) (SEQ ID NO:2) and (253)GGC TTCTCGAAGT ACATAAGCGG ATAACGGATC (221) (antisense) (SEQ ID NO:3), SHA was performed by cycle-sequencing with antisense primer, (95) GGGAG TATAAAACAG GCGTACAAGG GTACC (66) (SEQ ID NO:4) as described above.

Analysis of the 3'-end

A similar approach was used to amplify 3'-terminal region for both type 1 and type 2. cDNA was made with a primer containing oligo(dT) at its 3'end: AGCTGATCGATGGGCTACCA TGCGTACCCT TTTTTTTTT TTTTTTTTT (SEQ ID NO:5). After PCR amplification with the primers (7324) GCTCCCA GAGTACTCAA CATTGTACCG CCGTTG (7356) (sense) (SEQ ID NO:6) and AGCTGATCGA TGGGCTACCA TGCGTACCCT (anti-sense) (SEQ ID NO:7). SHA was done by cycle-sequencing with the sense primer (7361) GACTCATTTT AGTAACCCTA CCTCAGTCGA ATTGG (7395) (SEQ ID NO:8).

MAPREC assay for reversions

Quantitation of each mutation identified by SHA was performed using the MAPREC assay with the primers and the restriction enzymes listed in Table 1 for type 1 and Table 2 for type 2. Restriction digests of radiolabeled PCR products were separated by polyacrylamide gel electrophoresis for quantitation in a Betascope B603 Blot Analyzer (Betagen). To evaluate quantitative performance of MAPREC the specificity of each of the tests and additivity of revertant and attenuated nucleotides at each position were examined. Primer pairs were specifically designed to allow reciprocal testing to be done in parallel (i.e., both mutant and normal sequence-specific digests from the same PCR product).

The experiments summarized in Tables 3, 4, and 5 included PCR products made from a plasmid containing the full cDNA copy of Sabin 1 (Table 3) and Sabin 2 (Tables 4 and 5) RNA and cDNA samples derived from high-passage level viruses, serving as negative and positive controls for mutant quantitation at each position. The percentage of mutant-type sequence determined for the plasmid at each tested position indicates the amount attributable to nonspecific factors such as background radioactivity in the gel and/or base misincorporation during PCR (Lu et al., 1993). In general for the tests described in Tables 3, 4 and 5, this negative control value ranged from 0%–0.5%, indicating a high degree of specificity for the MAPREC tests. The negative control values for positions 964, 1971, and 4346 sometimes fell in the range 0.5%–0.8%, and for position 4706 the value ranged from 0.4%–2.2%. For each tested position, the amount of Sabin-type sequence determined in the plasmid (performed routinely as a positive control) typically was observed to be 95% or greater, except for position 2872 which was about 90%. The amounts determined for Sabin- and mutant-type sequences in the experimental samples, including cell culture passages and vaccine lots, were found to be additive except in the tests for positions 2908 and 3364 described below.

Monkey neurovirulence test

MNVT was performed by intraspinal inoculation of rhesus monkeys according to the World Health Organization procedure (1990) and the mean lesion scores (MLS) were calculated after histologic examination of the central nervous system sections (21 C.F.R. §630.15, 1994). Twelve monkeys were used for each virus sample.

Accumulation of reversions in the 5'-UTR in type 1

In type 1, nucleotides 480 and 525 are base paired in a stem and loop structure of the F-domain of the 5'-UTR (Skinner et al., J. Mol. Biol. 207:379–392 (1989)) which is a part of the internal ribosome entry site (IRES) (Muzychenko et al., Virus Res. 21:111–122 (1991)). Mahoney, a wild-type strain, has 480-A:525-U configuration, while attenuated type 1 Sabin strain has a weaker 480-G:525-U base pair impairing protein synthesis initiation. In revertant strains stronger base pairing and in vitro mRNA activity of the viral RNA can be restored either by direct reversion to A at nucleotide 480 or by mutation to C at nucleotide 525. The present examples determined the kinetics of selection of revertants at 34 and 37° at these sites in primary AGMK culture, and two continuous cultures derived from it, Vero and CV-1. At the first two passages both mutations accumulated in all three types of cell culture. At the higher passages, 525-C continued to accumulate in Vero cells while the amount of 480-A revertants decreased. In CV-1 cells the opposite trend occurred, and 480-A rapidly took over. In AGMK cells the rate was slower, and both mutations accumulated gradually, with 480-A accumulating somewhat faster than 525-C.

The selection of neurovirulent reversion at nucleotide 472-C of Sabin 3 strain was increased in overconfluent cultures. Upon passage of Sabin 1 virus in overgrown Vero cultures (i.e., infected 3 days after reaching confluence), A:U pair was rapidly selected instead of G:C pair in underconfluent culture, showing that the status of this cell substrate can affect not only the rate of accumulation, but also the type of reversion.

480-A and 525-C revertants in type 1 OPV

More than 50 lots of type 1 OPV made by seven manufacturers were tested for the proportion of these revertants, as well as Sabin Original (SO) stock, and some reference vaccine samples (Table 6). It is clear that both reversions accumulate during the manufacturing process, since the content of both revertants increased from 0.26% in the SO virus to 0.5% in the SO+2 reference and 2.69% in the SO+3 reference. Because reversions at either complementary nucleotide 480 or 525 restore the secondary structure and increase monkey neurovirulence, it is preferred that their total amount should be considered for assessment of vaccine quality. In commercial monopools made by different manufacturers, and which passed the MNVT, percentage of 480-A plus 525-C ranged from 1.1 to 2.7%.

Reversions at nucleotides 480 and 525 and monkey neurovirulence

There was no single vaccine lot among those available to be tested that would reliably fail the MNVT. One type 1 OPV lot originally failed the MNVT but passed several repeated tests, and therefore can be regarded as a borderline vaccine lot. The content of both 480-A and 525-C mutants in this lot was noticeably increased (total of 4.1%). In order to study the impact of revertants on monkey neurovirulence experimental samples with increased content of revertants were prepared and tested in monkeys. Results of these tests are presented in FIG. 1 along with the data on commercial vaccine lots. It shows that the MLS increased when the content of 480-A+525-C exceeded 5–10%. However, further rise in revertant content did not significantly increase the MLSs.

Identification of other selectable mutations in type 1

Changes at nucleotides other than 480 and 525 may accumulate in Sabin 1 strain during passaging in cell culture and may alter the attenuated phenotype. This possibility was addressed by looking at all mutations that have previously been associated by others with either in vivo or in vitro changes of the $rct_{40}$ and neurovirulence phenotype. In addition to nucleotides 480 and 525, five of these sites (nucleotides 2438, 2741, 2795, 203, and 7441) were analyzed by MAPREC assays in Sabin 1 virus serially passaged in AGMK and Vero cells and in commercial vaccine monopools. Accumulation of only two of these mutations were detected at nucleotides 6203 and 7441, mostly in the Vero-passaged virus. While there was no detectable reversion at nucleotide 6203 in vaccine lots or in AGMK-passaged virus at both 34 and 37°, in Vero cells about 2% of 6203-U mutants could be detected after 10 passages. The G to A reversion at nucleotide 7441 changes the 3'-ultimate nucleotide immediately adjacent to the polyA tract. Similar reversion was previously found in Sabin 3-derived virus isolated from vaccinees and temperature-resistant in vitro derivatives of Sabin 1. This reversion did not show a consistent trend for accumulation in AGMK cells, but was clearly accumulating after passage in Vero cells; in commercial vaccine lots its content did not exceed 0.5%.

Because some weak neurovirulence determinants of type 1 poliovirus are scattered along the entire genome, an extensive survey of the whole genome is needed in order to find all possible sites at which mutations accumulate. Mutations are occurring randomly at approximately equal frequencies at all sites of the poliovirus genome, but unless they provide replicative advantages to the virus, they remain at low levels and are not detectable in the MAPREC assay. To identify all the sites in Sabin 1 that consistently accumulate nucleotide changes beyond the background level, vaccine virus was serially passaged 10 times in two cell cultures, AGMK and Vero, at both optimal and supraoptimal temperatures (34° and 37°) in order to amplify consistently selectable mutations to a detectable level. Passaging was performed at a high m.o.i. to prevent "bottle-neck phenomenon," i.e., selection of incidental mutations because of a limited number of viral particles in the inoculum. At this m.o.i. cytopathic effect occurs after 48 hr, similar to what happens during vaccine manufacturing. RNA of these high-passage viral samples was reverse transcribed and amplified by PCR to give 11 overlapping DNA segments which spanned the entire viral genome. A special template-extension method was used to amplify the 5' and 3' ends of RNA molecule, which could not be amplified directly because they were used for primer binding. A total of 13 DNA segments generated by PCR were analyzed by cycle-sequencing with Taq DNA-polymerase, and autoradiographs were carefully inspected for the presence of minor bands suggesting a heterogeneity of nucleotide sequence. Each mutation identified by this SHA was independently confirmed and quantitated by the MAPREC assay. This SHA proved to be very sensitive; in some cases heterogeneities were detected at a level below 1%, while in others, sensitivity was lower due to the presence of "strong stop" bands on sequencing gels. Table 3 shows that, in addition to reversions at complementary nucleotides 480/525 described above and some heterogeneity at nucleotide 7441, the only site where minor heterogeneity was detected in AGMK-passaged virus was nucleotide 612. U to C mutation at nucleotide 612 slowly accumulated, and after 10 passages was present at a level not exceeding 2%. No 612-C was detected in commercial vaccine lots.

In contrast, virus passaged in Vero cells accumulated at least five additional mutations in the coding region, two of them being silent mutations (nucleotides 1123 and 1141) and three missense mutations in VP2, 2C, and 3Dpol genes (nucleotides 1449, 4944, and 6203, respectively). The latter mutation was described above; mutations at nucleotides 1449 and 4944 rapidly accumulated in Vero cells, almost completely replacing the original nucleotide after 10 passages, while in AGMK the rate of accumulation was much slower, and after 10 passages at 37° C. virus sample contained only 1.1% 1449- G and 0.15% 4944-G. These mutations were not detected in vaccine lots.

Taking into account a high sensitivity of sequence heterogeneity screening and the fact that it was performed on the virus grown under exaggerated conditions favoring viral changes (supraoptimal temperature and very high passage level, significantly higher than that allowed for vaccine manufacture) and still yielded a reproducible pattern of mutations, the majority of mutations in Sabin I genome that provide selective advantage to the virus, and may accumulate during vaccine manufacturing have been identified.

Upon virus cultivation in AGMK cells there was a remarkably low number of unstable nucleotides. Besides complementary nucleotides 480 and 525 described before, there were only two more sites, 612 and 7441, at which some minor mutant accumulation occurred. The effects of these mutations remain to be elucidated. 612-U is base-paired to A of the AUG codon within the box B element which is believed to be an essential component of the poliovirus IRES (Pilipenko et al., Cell 68:119–131 (1992)). It may be speculated that secondary structure disruption caused by this U to C mutation facilitates interaction with ribosome and/or initiation factors. G to A reversion at nucleotide 7441 can weaken the hairpin at the 3' end of polio RNA which may participate in initiation of RNA synthesis.

The situation with Sabin 1 virus grown in Vero cells was more complicated. It accumulated five additional mutations, two of which are silent and three of which are missense mutations. From many studies such as described herein, selection of silent mutations seems to be a common phenomenon in all three types of poliovirus. It is highly unlikely that this selection is driven by the codon preference but it may be due either to alteration of the RNA secondary structure or to some direct interaction with cellular components. One of the three missense mutations, C to U transition at nucleotide 6203 that changes histidine-73 to tyrosine in virus RNA replicase, was originally identified in temperature-resistant derivatives of Sabin 1, implicated in increased neurovirulence, and later found in recombinant isolates from cases of vaccine-associated paralysis (Furione et al., Virology 196:199–208 (1993)). Two other missense mutations, A to G transitions at nucleotides 1449 and 4944, change glutamine to arginine at amino acids 166 of VP2 and 238 of 2C, respectively.

Lower genetic stability of Sabin strains grown in Vero cells compared to AGMK cells was observed for all three types of OPV (Chumakov et al., Journal of Medical Virol. 42:79–85 (1994)), and probably reflects the fact that Sabin strains were derived in primary cultures of monkey kidney cells and therefore are better adapted to this substrate. These findings indicate that any switch to a new cell substrate is preferably accompanied by additional studies of the composition of the viral population to document and assess any changes in the vaccine. Some of the nucleotide changes may not increase the neurovirulence of the vaccine but may actually introduce desirable qualities into the vaccine, such as increased genetic stability or replicative capacity.

Identification and quantitation of unstable sites in Sabin 2 genome

Screening by SHA identified 15 new sites that contain sequence heterogeneities in the virus passages-in AGMK or Vero cells at 34° C. and 37° C., including nine samples later shown by MAPREC to contain less than 16% of mutations and in one sample less than 1%. Results of this search and quantitation of amounts of each detected mutation are summarized in Table 4. The percentages shown for the mutations at each position are the values determined in the tenth virus passage. For virus passaged in AGMK cells at 34° C. and 37° C., 5 and 2 positions, respectively, were observed to have mutations present at a levels in excess of 1%. For virus passaged in Vero cells at 34° C. and 37° C., 6 and 13 positions, respectively, were observed to have mutations present at levels in excess of 1%. The prevalence and accumulation of these mutants over the course of the ten passages is described below.

Several other mutations were previously found by Pollard et al. (1989) in Sabin-derived strains isolated from vaccinees. These mutations were quantified in cell culture passages by MAPREC (Table 5). For technical reasons, the mutation at nucleotide 4076 could not be reliably detected at levels below 3–4%. Presence of the 2909-C mutation makes it impossible to test for an adjacent 2908-G mutation on the same molecule using the MAPREC primers and restriction enzymes indicated in Table 2. Therefore, the presence of 23.9% of 2909-C mutation in virus passaged in AGMK at 34° C. prevents accurate quantitation of 2908-G in this sample, as only those molecules having 2908-G and 2909-T would be detected by the test for 2908-G. However, since both of these mutations change the same codon, the sum of 2908-G and 2909-C determined using these primers reflects the total amount of mutants in the codon for amino acid 143 of VP1, and the two are combined (2908+2909) for the purpose of discussion. Small levels of mutations at nucleotide 437 were also detected in virus grown at 37° C. in both AGMK and Veto cells. Mutations at positions 398, 685 and 868 could not be detected at a significant level in these passages.

Mutant accumulation during passages in cell cultures of type 2

To see whether the above sequence heterogeneities represent mutations that are consistently selected, the kinetics of their accumulation in passages were studied. In the virus grown in AGMK cells at 34° C., four sites showed consistent accumulation of mutations, at positions 869, 1971, 2908/2909, and 3364. In the virus grown in AGMK cells at 37° C., consistent accumulation of mutations was observed at positions 437, 481, and 2908/2909. The virus grown in Vero cells at 34° C. had six selectable mutations (nucleotides 481, 2908/2909, 3364, 3895, 4452, and 4943) and 14 selectable mutations at 37° C. (nucleotides 437, 481, 491, 698, 964, 1122, 2872, 3369, 3740, 3766, 3895, 4346, 4452, and 4943). The kinetics of accumulation of mutants in the virus passaged in AGMK cells at 34° C. was determined. In most cases mutations accumulating in AGMK cells at 37° C. and in Vero cells at both temperatures demonstrate similar kinetics. In some cases mutations that accumulated significantly in one cell type and at one temperature were also detected in samples of virus passaged on other cell type or temperature but only at a very low level. Examples where the mutation was detected but did accumulate significantly are 3766-A in AGMK cells at 34° C. and 4346-C in AGMK cells at 34° C. and 37° C. and 4346-C in Veto cells at 34° C. (Table 4).

At some genome sites of the virus passaged in Vero cells, almost complete substitution of the original nucleotide by the mutant (nucleotides 2909, 3895, and 4452) was observed. In contrast, the virus passaged in AGMK cells did not accumulate mutations at any nucleotide in excess of 24%. In virus passaged ten times in AGMK cells at 34° C., three mutations (at nucleotides 869, 1971, and 2909) accumulated in the range of 12%–24% and a mutation at position 3364 accumulated to a very low level (<2%), while a low level of mutation at position 481 was present throughout the passages and did not accumulate. The mutation at nucleotide 2908 affecting the same amino acid as the mutation at 2909 (see above) may also have accumulated to a very low level, but could not be quantified due to the presence of the mutation at adjacent nucleotide 2909.

At nucleotide 3364, a decrease in the Sabin-type sequence was observed during passage of the virus in AGMK cells grown at 34° C. Because there was no corresponding increase detected in the 3364-A mutation (observed to accumulate during virus passage in Vero cells at 34° C.), and since no evidence was found of other base substitutions at this site, adjacent mutations that might interfere with the MAPREC test due to the specificity of the restriction enzyme used to detect 3364-G were analyzed. An additional mutant was identified at nucleotide 3365 (G substituting for Sabin-type A), changing Glu-295 in VP1 to Gly, instead of Lys resulting from the mutation at 3364. The mutation reached a level of <1% during virus passage in AGMK cells at 34° C. and was not observed in passages from other culture conditions. The loss of Sabin-type sequence at position 3364 observed during passage of the virus in AGMK cells grown at 34° C. approached 10%, and thus can be explained only partially by the adjacent mutation at position 3365. Other undetected heterogeneities in the vicinity of nucleotide 3364 might also have contributed to the lack of additivity at this site in the virus propagated in AGMK cells at 34° C.

Impact of cell culture confluence on accumulation of the 481-G revertant in type 2

The influence of the substrate on specific accumulation of the 472-C mutation in type 3 poliovirus included effects attributable to cell density of the culture monolayer. To examine whether this was also true for position 481 of the type 2 genome, cultures of Vero cells were infected at 95% confluence or three days after reaching confluence. As observed for 472-C in type 3 poliovirus, the mutation at nucleotide 481 in type 2 poliovirus accumulated more rapidly in overconfluent cultures.

Mutations in commercial monopools of type 2 OPV

Since reversion at nucleotide 481 was reported to play a significant role in neurovirulence in monkeys, the presence of 481-G was tested in more than 50 samples of OPV 2 made by seven manufacturers as well as in several virus reference samples and seed viruses. The results are shown in Table 7, with results for samples from individual manufacturers combined as means. The mutant content in the individual samples ranged from 0.2%–1.1%. All samples passed the MNVTs.

To see whether other sequence heterogeneities described above are present in OPV, commercially prepared monopools of Sabin 2 virus were tested for the mutations observed to accumulate in virus passaged in AGMK at 34° C., conditions similar to those used for vaccine production. MAPREC tests for mutations at positions 869, 1971, and 2909 were performed on all available vaccine lots. A few lots were also tested for mutations at nucleotides 2908 and 3364. The mutation observed at position 3766, while detectable at a level of 1.5% in passage ten (Table 4), was not detected in earlier passages and was not tested in the vaccines. All the vaccine lots contained small amounts of revertants at all the sites tested. The content of 869-U mutation ranged from 0.1% to 0.9% in monopools made by all manufacturers except for one monopool which contained 4.4%. The content of 2909-C mutation ranged from 0% to 0.5%, and 1971-C from 1.5% to 2.9%. A value of approximately 0.9% was obtained for 1971-C in the plasmid control, presumably due to nucleotide misincorporation during PCR, so the actual amounts of 1971-C in the vaccines are presumably lower. Thus vaccines made by different manufacturers showed specific patterns of these mutations that probably reflect differences in working seed viruses and growth conditions.

Neurovirulence of type 2 in monkeys

Virus samples from passage levels four and ten in AGMK cells grown at 34° C., and passage levels five, seven, and ten in AGMK cells grown at 37° C., were tested for neurovirulence in monkeys. The results are shown in Table 8, with levels of mutations observed at positions where heterogeneities were detected. It appeared that no mutations accumulating in Sabin 2 virus passaged in AGMK cells at 34° C.

(mutations at nucleotides 869, 1971, and 2908+2909) present at levels ranging from 10 to 27% contributed to increased monkey neurovirulence. However, an association between increased levels of 481-G mutant and higher histological lesion scores was apparent (FIG. 2). The threshold level for the effect of 481-G revertants accumulating in AGMK cells at 37° C. and in Veto cells at 34° C. and 37° C., seems to be above 2%, and the sample with approximately 4% revertants failed the MNVT (Table 8). This threshold level is higher than that for 472-C revertants in Sabin 3 virus, suggesting that contribution of 481-G to monkey neurovirulence is smaller.

The patterns of mutations that accumulate in different cell cultures and at different temperatures were specific for a given set of conditions. The number of selectable mutations and the rate of their accumulation was higher in Vero cells compared to AGMK cells. The same trend was observed for type 1 OPV and for type 3 OPV. These findings can be important for vaccine production, since Veto cells are now a substrate of choice for some vaccine manufacturers. This requires even more strict control of the manufacturing conditions when Veto cells are used and more detailed study of the role in neurovirulence of numerous virus mutations accumulating in Vero cells.

As with Sabin 1 and 3 polioviruses, higher temperature increases accumulation of mutants in Sabin 2 virus. However, some mutations, e.g., at nucleotides 869, 1971, 2909, and 3364, are selected faster at 34° C. than at 37° C. As with Sabin 1 and Sabin 3 polioviruses, consistently accumulating mutations in Sabin 2 occur in both untranslated and protein-coding regions of the genome, and in the protein-coding region they can be either missense or silent mutations.

The mechanisms underlying the selection of missense mutations are unclear but allow reasonable speculation. Mutation at position 869 changes Ala to Val at amino acid 40 of VP4. This amino acid may play some role in assembly or uncoating of the virus capsid, since a mutation at nucleotide 868, changing Ala to Thr, was found in isolates from vaccinees (Pollard et al., 1989), suggesting that Ala at this position may reduce fitness of the virus. Another mutation accumulated at nucleotide 2909 in Sabin 2 virus grown in AGMK cells, changing Ile-143 in VPI to Thr, while a mutation at 2908 in the same codon, accumulating primarily in the virus grown in Vero cells, gives Val. Both mutations were previously found in virus isolated from vaccinees (Pollard et al., 1989; Macadam et al. Virology 192:18–26 (1993)) found that Ile-143 in Sabin 2 virus changes to Val, Thr, Asn, or Ser in stool isolates from vaccinees. The accumulation of Val-143 and Thr-143 was observed in both AGMK and Vero cells. At 34° C. the predominant type of mutation was Thr-143 (2909-G to A mutation), while at 37° C. Val-143 (2908-A to G mutation) prevailed. It is noteworthy that all the mutations are located in the left half of the genome, and no mutation accumulated in P3 region. The mutations were found in the capsid region (in VP4 and VP1), and in P2 proteins, including two mutations in 2A, which may affect either proteolytic activity of this protein, or its function in initiation of translation.

The newly found selectable mutations were assessed for effect on neurovirulence of Sabin 2 strain. Virus samples containing various amounts of several mutations were selected for neurovirulence tests in monkeys. At least some of these mutations, including mutation of Ile-143, are unlikely to increase neurovirulence. Of four mutations that were identified in Sabin 2 virus passaged 10 times in AGMK cells at 34° C., one mutation was present at a level of less than 4%, and three others at levels of 10–24%. This virus sample passed the MNVT with a low histological lesion score, showing that none of these mutations, in the amounts present, increased neurovirulence. In contrast, the virus passaged at 37° C. accumulated reversion at nucleotide 481-G to a level of 7.4% and failed the monkey test. In addition 437-C mutation accumulated to a level of 5% by passage ten. The other mutations that accumulated in virus passaged in AGMK at 34° C. to even higher levels without increasing neurovirulence of the virus, and cannot be used to predict the results of the MNVT. However, determination of the specific levels of each of these mutations can still be useful for monitoring the consistency of vaccine production.

The monkey neurovirulence data imply that effects of the mutations at amino acid 143 of VPI on neurovirulence in monkeys cannot be very strong, since a virus sample with approximately 24% of 2909-A and 3% 2908-G passed the MNVT with a low histological lesion score. Studies performed in monkeys by Macadam et al. (1993) also demonstrated no neurovirulent effect of the mutation at this site. Therefore, despite the observation that Ile-143 is clearly selected against both in vivo and in vitro, it appears that it increases neurovirulence of the virus in mice but not in monkeys.

The threshold of the most important reversion at nucleotide 481 is higher than the threshold for 472-C revertants in Sabin 3 virus for which the sample with 1.2–1.3% of revertants fail the MNVT. For Sabin 2 virus the threshold is somewhere between 1.7% and 3.7% of 481-G. No monopool of type 2 OPV among those available to be tested failed the MNVT and the above information was obtained with experimental samples. Considering that most commercial vaccine lots have less than 1% of 481-G, there appears to be a wide margin of safety for OPV of type 2, which explains why it very rarely, if ever, fails the MNVT. Therefore, the MAPREC test might be more sensitive for monitoring the consistency of type 2 OPV production than the MNVT.

Influence of multiplicity of infection and temperature on types 1, 2 and 3

To study the accumulation of 472-C revertants, four consecutive passages of type 3 OPV in AGMK cells were performed using either low m.o.i. (0.01 TCID$_{50}$/cell) or high m.o.i. (1–2 TCID$_{50}$/cell). Infected cultures were incubated either at optimal (34° C.) or supraoptimal (37° C.) temperature. At 37° C. and at low m.o.i. the rate of mutant accumulation was higher. Though selection of mutants was consistently faster at low m.o.i., there was much greater variability between experiments at this m.o.i., and therefore performed further passages only at higher m.o.i. In addition, virus growth conditions close to those used for vaccine manufacturing were utilized. In a typical experiment complete cytopathogenic effect (c.p.e.) developed in about 48 hours after infection with high m.o.i., which is close to the time of virus replication during the vaccine manufacturing.

The accumulation of revertants at positions 480 and 481 of type 1 and 2 also was faster at 37° C. compared to 34° C. Low amounts of these revertants were detected in every lot of commercially produced type 1 and type 2 vaccines at a level about 1%.

Influence of different cell substrates

Two substrains of type 3 Sabin OPV were used in these experiments. The first one was Sabin Original (SO) strain, which was used for OPV manufacturing until the middle of 1980s, and the second one was RSO (Pfizer) strain, which was rederived from SO by RNA-plaque purification and is currently being used by most manufacturers of OPV. Different cell substrates which are currently used or proposed for use in OPV manufacturing, as well as some cell cultures commonly used for poliovirus growth, were tested. Cells were infected at high m.o.i. (1–2 $TCID_{50}$/cell) with the above viruses at a passage level two (SO+2 and RSO+2) and incubated either at optimal (34° C.) or supraoptimal temperature (37° C.) until the complete c.p.e. occurred. Four consecutive passages in each cell substrate were made in each experiment. Three independent series of passages were carried out in AGMK, Vero, and WI-38 cells; MAPREC determination was done three times with each sample. Rates of mutant accumulation varied in different cell substrates, with the highest rates observed in Vero, CMK, and AGMK, and the lowest rates in WI-38 and HEp-2. Veto cells displayed the highest temperature effect, where mutant accumulation was up to 100 times higher at 37° C. than at 34° C. Other cell substrates also showed greater mutant accumulation at 37° C. than at 4° C. In most cases the rate of 472-C mutant accumulation was higher in the SO strain than in the RSO strain. It should be noted that there is some variability between experiments suggesting that the selection process, which is stochastic in its nature, may be affected by other factors and parameters of virus growth which may not always be kept constant. The rate of mutant selection seems to be inversely related to the rate of virus multiplication, as determined by the time of maximum c.p.e. HEp-2 cells, with the lowest rate of selection, replicate virus faster than Vero cells, which have the highest selection rate. Vero cells, which demonstrate the maximum temperature bias in the rate of 472-C accumulation, also show the greatest difference in maximum c.p.e. time at 37° C. and 34° C.

MAPREC analysis of type 1 and type 2 OPV passaged in Vero cells was performed and it was found that mutations at these positions also rapidly accumulated in cell culture. Thus, instability both in vivo and in vitro is an intrinsic property of these sites in the 5'-noncoding region of OPV genomes of all three types.

Influence of culture confluence

Substrate influence on mutant selection suggests that cellular factors affect the rate of mutant accumulation. Overgrown cultures, which were infected 3 days after reaching confluence, and cultures which were almost confluent, but still had about 5% of open area, were compared. The rate of 472-C mutant accumulation in the SO strain passaged in AGMK cells was higher in overgrown cultures than in subconfluent ones. The same trend was observed with the RSO strain in AGMK cells and was also observed in Vero cells.

One possible explanation of the effect of culture confluence is that the number of cells in overconfluent cultures is higher, and consequently m.o.i. is lower. As a result more rounds of virus replication occur in overgrown cultures and the selection rate is higher. The number of cells in the overgrown cultures was estimated to be about two times higher. Even though this can potentially contribute to the observed difference in the mutant selection rate, there is direct evidence showing that more specific factors are involved. Determination of the content of another selectable mutation, C to U reversion at 2493 (Chumakov et al., 1992a), performed on the same samples of RSO strain passaged in AGMK and Vero cells, revealed no effect of cell confluence on the rate of 2493-U selection.

Therefore the effect of culture confluence in type 1 is specific for selection of 472-C revertants, and thus cannot be explained solely by the difference in the number of virus replication cycles which should affect selection of both mutations.

Thus, sensitive methods for the quantitation of mutants can be used to determine the choice of the cell substrates and manufacturing conditions and evaluate new vaccine strains with increased genetic stability. Cell substrates can thus be found or engineered which would select revertants at a much lower rate than the currently used primary cultures of monkey kidney cells or continuous Vero cultures.

Rapid selection of revertants at positions 480 and 525, 481 and 472 in OPV of types 1, 2 and 3 during passages in vitro and in vivo suggests that each of these mutations attenuate poliovirus by the same or similar mechanism which involves some reduction in replication competence. Attenuating mutations in the F domain of the 5'-untranslated region of all three types of OPV decrease the ability of poliovirus RNA to direct protein synthesis in vitro. The RNA domain F is believed to be involved in the interaction with protein factors mediating the ribosome binding during internal initiation of protein synthesis. These mutations may destabilize the secondary structure of this RNA domain and reduce the affinity of poliovirus RNA to initiation factors.

The data demonstrate that cell substrate influences the rate of 472-C revertant selection. The lowest rate was observed in human HEp-2 cells and diploid fibroblasts WI-38, used by some manufacturers for poliovirus vaccine production. Cell cultures derived from monkey kidneys which are currently used for vaccine manufacturing (AGMK and Vero) selected mutants at a higher rate. A direct method for determination of mutant selection rate would be valuable for making the optimal choice of the cell substrate. The apparent influence of cell substrate on the rate of mutant accumulation suggests that cellular factors are involved in the selection process. The properties and abundance of initiation factors in different cells can affect the competition between RNAs of attenuated and revertant strains. If these factors are abundant, both attenuated and revertant RNAs would be able to bind them and initiate protein synthesis at similar rates. If these factors are in short supply, revertant RNA with a higher affinity for these factors can outcompete vaccine RNA. Thus, the difference in selection rates in different cultures may be explained by the difference in abundance or affinity for these factors in cell cultures. The same hypothesis can be used to explain the effect of culture confluence. It is important to note that the effect of cell density is specific for the selection of mutation at position 472, because unlike the latter mutation, the rate of 2493-U selection was not influenced by the level of culture confluence. Therefore it cannot be explained solely by the small difference in the number of cells in these cultures which would effectively reduce m.o.i. in overgrown cultures. A role for cellular factors in mutant selection is also supported by the response of different cultures to the elevated temperature.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

TABLE 1

PCR PRIMERS AND RESTRICTION ENZYMES USED TO QUANTITATE MUTATIONS BY MAPREC

| SEQ ID NO: | Nucleotide | Primer polarity | Primer name | Primer sequence | Restriction enzymes (vaccine: revertant) | Mutation type (vaccine: revertant) |
|---|---|---|---|---|---|---|
| 9 | 480 | Sense | pS-1/453 | (421)AGCCTATTGG GCTACATAAG AATCCTCCGG CCC(453) | AluI:AvaI | 480-G:480-A |
| 10 | | Antisense | pA-1/482 | (513)CGACAGGCCA ATCACTGGTT TGTGACCACC AG(482) | | |
| 11 | 525 | Sense | pS-1/516 | (485)GTGGTCACAA ACCAGTGATT GGCCTGTCGT AA(516) | BspEI:ScrFI | 525-U:525-C |
| 12 | | Antisense | pA-1/527 | (560)AACACGGACA CCCAAAGTAG TCGGTTCCGC TCCG(527) | | |
| 13 | 612 | Sense | pS-1/611 | (578)GGCTGCTTAT GGTGACAATC ACAGATTGTG AGCA(611) | —:Bsp 1286I | 612-U:612-C |
| 14 | | Antisense | pA-1/623 | (657)GATAATGAAT CTCACTTTCA CCGGATGGCC AATCC(623) | | |
| 15 | 1123 | Sense | pS-1/1112 | (1081)CAGCGAAGCC AATCCAGTGG ACCAGCCGAC AG(1112) | AatII:PflMI | 1123-C:1123-U |
| 16 | | Antisense | pA-1/1124 | (1157)GACACGGTGT CTAGCGTATA AAACCTGCAT GCACC(1124) | | |
| 17 | 1141 | Sense | pS-1/1139 | (1105)GCCGACAGAA CCAGACGTCG CTGCATGCAG GTTGT(1139) | AccI:RsaI | 1141-U:1141-C |
| 18 | | Antisense | pA-1/1151 | (1185)CACCACCCTC GCGACTCTTT CGTCCAAGAC ACGGT(1151) | | |
| 19 | 1449 | Sense | pS-1/1416 | (1382)TATCAAAATG CCAATCCTGG CGAGAAAGGA GGCAC(1416) | XcmI:MspI | 1449-A:1449-G |
| 20 | | Antisense | pA-1/1451 | (1485)TAATCCACCG GGCAGAACCT ACGGCCAGGT GATGT(1451) | | |
| 21 | 2438 | Sense | pS-1/2436 | (2407)GTCAGCGTGT AATGACTTCA GCGTGCGCTT(2436) | SfaNI:Fnu4HI | 2438-A:2438-C |
| 22 | | Antisense | pA-1/2451 | (2484)AACCCCTGTG CTAGCGCTTT TTGCTCTATA TGTG(2451) | | |
| 23 | 2741 | Sense | pS-1/2739 | (2701)GTCTAGCATA GAGTCTTTCT TCGCGCGGGG TGCATACGT(2739) | HaeIII:AflIII | 2741-G:2741-U |
| 24 | | Antisense | pA-1/2751 | (2484)CTTATTCTTG GTGGAAGCTG AGTTATCCAC GG(2751) | | |
| 25 | 2795 | Sense | pS-1/2794 | (2761)CTCAGCTTC ACCAAGAATA AGGATAAGCT ATCT(2794) | —:PstI | 2795-A:2795-G |
| 26 | | Antisense | pA-1/2809 | (2840)TCCTCCGTAA CTGGACAGTA TCTTTATAAG TG(2809) | | |
| 27 | 4944 | Sense | pS-1/4943 | (4909)TCCCATGGCT ACTGAAATGT GTAAGAACTG TGATC(4943) | BclI:TaqI | 4944-A:4944-G |
| 28 | | Antisense | pA-1/4971 | (5005)GTCCATTAAT TGAATTGCCT TACCACACAC TAAAG(4971) | | |
| 29 | 6203 | Sense | pS-1/6201 | (6129)TCCCATGGCT ACTGAAATGTGTAAGAACTG TGATC(6201) | Bsp 12861: RsaI | 6203-C:6203-U |
| 30 | | Antisense | pA-1/6213 | (6246)GTCCATTAAT TGAATTGCCT TACCACACAC TAAAG(6213) | | |
| 31 | 7441* | Sense | pS-1/7440 | (7398)TGGGTCATAC TGCTGTAGGG GTAAATTTTT CTTTAATTCG GTG(7440) | —:HphI | 7441-G:7441-A |

*Assay for reversion at 7441 is based on amplification of polyA-containing DNA fragment using template-extension method (see Materials and methods)

TABLE 2

PRIMERS AND ENZYMES FOR MAPREC TESTS

| SEQ ID NO: | Site | Pair | Primer Sequence | Nucleotide in Sabin 2/ Restriction enzyme | Nucleotide in revertant/ Restriction enzyme |
|---|---|---|---|---|---|
| 32 | 398 | PS-2/396 | 5'-GCGTTGGCGGCCTACCTATGGCTAACGCCATAGGAC-3' | T Mae II | C Hga I |
| 33 | | PA-2/477 | 3'-GCCTTGTCCGCCAGCGCTTGGTCACTGACCGAAC-5' | | |
| 34 | 437 | PS-2/365 | 5'-CATTCCTCACCGGTGACGGTGGTCCAGGCTGCGTT-3' | T Nde I | C Nla III |
| 35 | | PA-2/438 | 3'-TaCTCAGGAGGCCGGGGACTTACGCCGATTAGGAT-5' | | |
| 36 | 481 | PS-2/465 | 5'-GCTACATAAGAGTCCTCCGGCCCCTGAATGCGGCT-3' | A Afl III | G Bsp1286 I |
| 37 | | PA-2/483 | 3'-TgCaCCAGCGCTTGGTCACTGACCGAACAGCATTGCGC-5' | | |
| 38 | 491 | PS-2/489 | 5'-TGAATGCGGCTAATCCTAACCACGGAACAGGtGaT-3' | G Nru I | A Bcl I |
| 39 | | PA-2/493 | 3'-CTTGGTCACTGACCGAACAGCATTGCGCGT-5' | | |
| 40 | 685 | PS-2/683 | 5'-GTCAGGTATACAACTGTTTGTTGGAACCgaTGTGT-3' | A Alu I | T Bcg I |
| 41 | | PA-2/743 | 3'-GATGTTACCCGCGGGTTCAAAGTAGTGTCTTTC-5' | | |
| 42 | 698 | PS-2/697 | 5'-CTGTTTGTTGGAACCACTGTGTTAGCTTTACTaCaC-3' | A Nla III | G Mae II |
| 43 | | PA-2/699 | 3'-AcATTGGTTAATTAGTTTTTGTTATGCTCCTATTTTG-5' | | |
| 44 | 868 | PS-2/867 | 5'-CAATTACTATAGGGACTCTGCAAGCAATGCA-3' | G Fnu4H I | T Nsi I |
| 45 | | PA-2/870 | 3'-TgCGTTCGTTCTAAAACGTGTTCTAGGCAGG-5' | | |
| 46 | 869 | PS-2/867 | 5'-CAATTACTATAGGGACTCTGCAAGCAATGCA-3' | C Fnu4H I | T Rsa I |
| 47 | | PA-2/870 | 3'-TgCGTTCGTTCTAAAACGTGTTCTAGGCAGG-5' | | |
| 48 | 964 | PS-2/962 | 5'-CTTATTAAGACCGCTCCCtTGCTAAACTCCCCAcA-3' | A Nla III | G Afl III |
| 49 | | PA-2/965 | 3'-AcCTCCGCACACCAATATCACTGTCCCATTACGTC-5' | | |
| 50 | 1122 | PS-2/1120 | 5'-AGGCAAATCCTGTAGACCAACCAACCGAGC-3' | C Bsp1286 I | T Cvn I |
| 51 | | PA-2/1124 | 3'-TcCATCGGCGCACGTCCAAGATGTGTAATCTATGG-5' | | |
| 52 | 1971 | PS-2/1968 | 5'-ACAAGTCAACGCAGAAACACAATGGACATG-3' | T Acc I | C Rsa I |
| 53 | | PA-2/1972 | 3'-TgTCAGCTCAgCTCGCTGTGCCGAGTGAGACTGTG-5' | | |
| 54 | 2872 | PS-2/2870 | 5'-CAAACTGGAATTTTTCACATATTCGAGATT-3' | G Drd I | A Mse I |
| 55 | | PA-2/2874 | 3'-GTACCTCCAGTGAAAACACCAGTGGAGTTTGATG-5' | | |
| 56 | 2908 | PS-2/2907 | 5'-GAGTTCACTTTTGTGGTCACCTCAAACTAC-3' | A not tested | G Mae II |
| 57 | | PA-2/2910 | 3'-AtTcCGTTTATTGCCTGTACGTAACTTGGTTCAAA-5' | | |
| 58 | 2909 | PS-2/2907 | 5'-GAGTTCACTTTTGTGGTCACCTCAAACTAC-3' | T Mse I | C Dde I |
| 59 | | PA-2/2910 | 3'-AtTcCGTTTATTGCCTGTACGTAACTTGGTTCAAA-5' | | |
| 60 | 3364 | PS-2/3363 | 5'-GTGTTGATTATAAAGATGGGCTCACCCCACTAttA-3' | G Mbo II | A Mse I |
| 61 | | PA-2/3366 | 3'-TcTCCCTAAaTGCTGAATACCTAAACCTGTGGTTT-5' | | |
| 62 | 3369 | PS-2/3367 | 5'-TGATTATAAAGATGGGCTCACCCCACTACCtGAAg-3' | G Mnl I | A EcoN I |
| 63 | | PA-2/3373 | 3'-AATTGCTGAATACCTAAACCTGTGGTTTTG-5' | A EcoN I | |
| 64 | 3740 | PS-2/3738 | 5'-GTGATTGTGGTGGCATACTTAGATGTCAACACGcG-3' | T Hph I | C Fnu4H I |

TABLE 2-continued

PRIMERS AND ENZYMES FOR MAPREC TESTS

| SEQ ID NO: | Site | Pair | Primer Sequence | Nucleotide in Sabin 2/ Restriction enzyme | Nucleotide in revertant/ Restriction enzyme |
|---|---|---|---|---|---|
| 65 | | PA-2/3742 | 3'-TATCCTTATTAGTGACGACCACCCCTTCCG-5' | | |
| 66 | 3766 | PS-2/3764 | 5'-ACACGGGGTGATAGGAATAATCACTGCTGGTGG-3' | G Bbs I | A Xmn I |
| 67 | | PA-2/3768 | 3'-TCtGAAgCAACGTAAAAGTCTGTAATCTCTGGACA-5' | | |
| 68 | 3895 | PS-2/3893 | 5'-GGTGCTGCATTTGGTAGTGGATTCACTCAACAAcT-3' | G Hph I | A Dde I |
| 69 | | PA-2/3897 | 3'-ACTATTTCAAAGGCTCGATTGGTCGTACCAT-5' | | |
| 70 | 4076 | PS-2/4076 | 5'-CCTTGGGTGCGACATCTCACCGTGGCAGTGGCTtA-3' | A Mse I | G Dde I |
| 71 | | PA-2/4147 | 3'-TGACgCCGTACATTACGACGTTTCCCTGACCTCA-5' | | |
| 72 | 4346 | PS-2/4344 | 5'-TACACCAATCTTGTCCAAGTCAAGAACATCAGtAG-3' | T Mbo I | C Acc I |
| 73 | | PA-2/4348 | 3'-AATAAGTTGTTACACGCCACCGATAGATAG-5' | | |
| 74 | 4452 | PS-2/4450 | 5'-CTAAAAGGATTCAAAAGCTGGAGCATACCATAAtTA-3' | T Ase I | C Dde I |
| 75 | | PA-2/4454 | 3'-TaCATGTCAAGTTCTCGTTCGTGGCATAACTCGGT-5' | | |
| 76 | 4943 | PS-2/4941 | 5'-ATGGCAATGGCTACTGAAATGTGCAAAAACTGTgAT-3' | A Bcl I | G Taq I |
| 77 | | PA-2/4946 | 3'-GTCGTTTGAAGTTTTCTACAACAGGAAATC-5' | | |

Note: Lower case letters show mismatched nucleotides that create or destroy restriction sites.

TABLE 3

RESULTS OF A SEQUENCE HETEROGENEITY ASSAY PERFORMED WITH HIGH-PASSAGE SAMPLES OF TYPE 1 OPV

| Position | Gene | Nucleotide | Codon | Amino Acid | AGMK 34° C. | AGMK 37° C. | Vero 34° C. | Vero 37° C. |
|---|---|---|---|---|---|---|---|---|
| 480 | 5'-UTR | G → A* | | | G > A | A = G | G >> A | G >> A |
| 525 | 5'-UTR | U → C | | | U > C | U > C | U > C | C >> U |
| 612 | 5'-UTR | U → C | | | U >> C | U >> C | Undetactable | Undetectable |
| 1123 | VP2 | C → U | GUC → GUU | Val, silent | Undetectable | Undetectable | C > U | C > U |
| 1141 | VP2 | U → C | UAU → UAC | Tyr, silent | Undetectable | Undetectable | Undetectable | C >> U |
| 1449 | VP2 | G → A | CAG → CGG | Gln → Arg | Undetectable | Undetectable | Undetectable | A > G |
| 4944 | 2C | A → G | CAA → CGA | Gln → Arg | Undetectable | Undetectable | G | G |
| 6203 | 3D | C → U* | CAC → UAC | His → Tyr | Undetectable | Undetectable | Undetectable | C >> U |
| 7441 | 3'-UTR | G → A* | | | G > A | G > A | A > G | G > A |

Note: Asterists denote true reversions to wild-type genotype (Mahoney).

TABLE 4

QUANTITATION OF MUTATIONS BY SEQUENCE HETEROGENEITY ASSAY IN SABIN 2 VIRUS AT PASSAGE LEVEL 10

| Site | Mutation Type | Gene | AGMK 34° C. | AGMK 37° C. | Vero 34° C. | Vero 37° C. | Control-plasmid |
|---|---|---|---|---|---|---|---|
| 491 | G → A | 5'-UTR | 0.13% | 0.86% | 0.10% | 9.29% | 0.11% |
| 698 | A → G | 5'-UTR | 0.21% | 0.27% | 0.16% | 43.85% | 0.14% |
| 869 | C → T Ala40 → Val | VP4 | 13.28% | 0.54% | 0.12% | 0.09% | 0.05% |
| 964 | A → G Ile83 → Val | VP4 | 0.73% | 0.82% | 0.23% | 13.59% | 0.47% |
| 1122 | C → t Silent | VP2 | 0.28% | 0.26% | 0.13% | 74.26% | 0.18% |
| 1971 | T → C Silent | VP3 | 11.85% | 1.12% | 1.58% | 1.25% | 0.70% |
| 2872 | G → A Asp131 → Asn | VP1 | 0.19% | 0.18% | 0.93% | 57.15% | 0.47% |
| 3364 | G → A Glu295 → Lys | VP1 | 1.76% | 0.00% | 65.11% | 0.20% | 0.04% |
| 3369 | G → A Silent | VP1 | 0.19% | 0.15% | 0.00% | 56.82% | 0.09% |
| 3740 | T → C Val119 → Ala | 2A | 0.45% | 0.44% | 0.36% | 47.61% | 0.14% |
| 3766 | G → A Glu28 → Lys | 2A | 1.55% | 0.07% | 0.52% | 75.56% | 0.14% |
| 3895 | A → G Gly22 → Ser | 2B | 0.17% | 0.00% | 2.07% | 80.94% | 0.20% |
| 4346 | T → C Ile75 → Thr | 2C | 1.78% | 1.59% | 1.29% | 46.97% | 0.46% |
| 4452 | T → C Silent | 2C | 0.35% | 0.78% | 1.39% | 87.92% | 0.18% |
| 4943 | A → G Gln275 → Arg | 2C | 0.45% | 0.23% | 41.64% | 23.42% | 0.30% |

TABLE 5

QUANTITATION OF MUTATIONS PREVIOUSLY FOUND IN ISOLATES FROM VACCINEES
(POLLARD, ET AL., 1989), AFTER 10 PASSAGES IN CELL CULTURES

| Site | Mutation Type | Gene | AGMK 34° C. | AGMK 37° C. | Vero 34° C. | Vero 37° C. | Control-plasmid |
|------|---------------|------|-------------|-------------|-------------|-------------|-----------------|
| 398  | U → C         | 5'-UTR | 0.00% | 0.59% | 0.00% | 0.09% | 0.00% |
| 437  | U → C         | 5'-UTR | 0.72% | 5.00% | 0.78% | 3.12% | 0.38% |
| 481  | A → G         | 5'-UTR | 0.64% | 7.42% | 1.41% | 10.46% | 0.15% |
| 685  | A → T         | 5'-UTR | 0.00% | 0.06% | 0.01% | 0.03% | 0.05% |
| 868  | G → A Ala40 → Thr | VP4 | 0.05% | 0.00% | 0.03% | 0.09% | 0.00% |
| 2908* | A → G Ile43 → Val | VP1 | 2.74% | 7.03% | 1.20% | 0.52% | 0.10% |
| 2909 | T → C Ile143 → Thr | VP1 | 23.87% | 2.30% | 92.08% | 0.57% | 0.35% |
| 4076 | A → G Lys82 → Arg | 2B | 3.98% | 1.64% | 2.09% | 2.87% | 2.22% |

*2908-G cannot be detected by this assay if 2909-C is present on the same RNA molecule

TABLE 6

CONTENT OF 480 AND 525 REVERTANTS IN TYPE 1 OPV

| Sample | | 480-A (%) | 525-C (%) | Total (%) |
|--------|---|-----------|-----------|-----------|
| Sabin original | | 0.09 | 0.17 | 0.26 |
| SO + 2 Reference | | 0.22 | 0.28 | 0.50 |
| SO + 3 Reference | | 1.45 | 1.24 | 2.69 |
| Manufacturer | No. of Lots | | | |
| A | 7 | 0.56 ± 0.23 | 0.61 ± 0.13 | 1.16 ± 0.36 |
| B | 10 | 0.66 ± 0.21 | 0.68 ± 0.10 | 1.33 ± 0.31 |
| C | 4 | 0.74 ± 0.08 | 0.61 ± 0.06 | 1.35 ± 0.14 |
| D | 2 | 1.06 ± 0.16 | 0.65 ± 0.02 | 1.71 ± 0.18 |
| E | 5 | 0.89 ± 0.31 | 0.87 ± 0.29 | 1.76 ± 0.61 |
| F | 1 | 1.29 | 0.94 | 2.23 |
| H | 20 | 1.23 ± 0.30 | 1.15 ± 0.21 | 2.38 ± 0.51 |

TABLE 7

CONTENT OF 481-G REVERTANTS IN TYPE 2 OPV

| Sample | Number of lots | 481-G |
|--------|----------------|-------|
| Sabin Original | 1 | 0.24 |
| WHO Reference | 1 | 0.29 |
| US Reference | 1 | 1.05 |
| Manufacturer | | |
| A | 8 | 0.43 ± 0.06 |
| B | 5 | 0.44 ± 0.11 |
| C | 8 | 0.44 ± 0.12 |
| D | 2 | 0.46 ± 0.04 |
| E | 4 | 0.47 ± 0.07 |
| F | 2 | 0.53 ± 0.22 |
| H | 15 | 0.61 ± 0.19 |

TABLE 8

RESULTS OF THE MONKEY NEUROVIRULENCE TEST OF EXPERIMENTAL SAMPLES OF OPV 2

| Sample | | Monkey test | | | | | Mutations | | |
|--------|---|-------------|---|---|---|---|-----------|---|---|
| | | Lesion Score | Pass/fail | 437-C | 481-G | 491-A | 869-T | 1971-T | 2908-G | 2909-C |
| NB-2 reference | | 0.49 | Pass | | | | | | | |
| AGMK passage | @ t° C. | | | | | | | | | |
| 4 | 34° C. | 0.66 ± 0.30 | Pass | 1.24 | 0.37 | 0.32 | 2.49 | 1.66 | 1.61 | 0.48 |
| 10 | 34° C. | 0.40 ± 0.26 | Pass | 0.72 | 0.64 | 0.13 | 13.28 | 11.85 | 2.74 | 23.87 |
| 5 | 37° C. | 0.59 ± 0.30 | Pass | 0.72 | 1.73 | 0.49 | 0.47 | 1.71 | 1.94 | 0.78 |
| 7 | 37° C. | 1.03 ± 0.59 | Fail | 2.00 | 3.71 | 0.41 | 0.51 | 1.66 | 5.57 | 1.20 |
| 10 | 37° C. | 1.42 ± 0.40 | Fail | 5.00 | 7.42 | 0.86 | 0.54 | 1.12 | 7.03 | 2.30 |

---

What is claimed is:

1. A method of classifying an unclassified live poliovirus type 2 vaccine which is attenuated by a G to A substitution at nucleotide position 481 as having an acceptable or unacceptable level of neurovirulence, comprising, prior to vaccine administration, the steps of:

a) selectively amplifying a region of an unclassified poliovirus type 2 vaccine genome containing nucleotide position 481 using selectively mismatched primers, whereby a restriction endonuclease site which includes nucleotide position 481 in the selectively amplified region is created by introducing a site-specific mutation into the amplified region;

b) digesting an amount of the amplified region with a restriction endonuclease that specifically cleaves the amplified sequences in revertant viruses which contain an A to G reversion at nucleotide position 481;

c) digesting an amount of the amplified region with a restriction endonuclease that specifically cleaves the amplified sequences in nonrevertant viruses which contain an A at nucleotide position 481;

d) quantifying the percentage of revertant viruses in the unclassified vaccine; and e) comparing the percentage of revertant viruses in the unclassified vaccine to the percentage of revertant viruses in an accepted reference vaccine which can pass the monkey neurovirulence test utilized by the World Health Organization, an unclassified vaccine with a higher percentage of A to G revertant viruses than in the reference vaccine being classified as unacceptable and an unclassified vaccine with an equal or lower percentage of A to G revertant viruses than in the reference vaccine being classified as acceptable.

2. The method of claim 1, wherein the amplification is by the polymerase chain reaction.

3. A method for classifying an unclassified live poliovirus type 2 vaccine which is attenuated by a G to A substitution as having an acceptable or unacceptable level of neurovirulence, comprising the steps of:

a. quantifying the percentage of revertant viruses contained in the unclassified vaccine prior to administration by testing for the presence of an A to G reversion nucleotide position 481, and b. comparing the percentage of revertant viruses in the unclassified vaccine to the percentage of revertant viruses in an accepted reference vaccine which can pass the monkey neurovirulence test utilized by the World Health Organization, an unclassified vaccine having a higher percentage of the A to G reversion than in the reference vaccine being classified as unacceptable and an unclassifed vaccine having an equal or lower percentage of the A to G reversion than in the reference vaccine being classified as acceptable.

4. A method for determining the suitability of a cell culture for production of a poliovirus type 2 vaccine which is attenuated by a G to A substitution at nucleotide position 481, comprising the steps of:

a. culturing an attenuated live poliovirus type 2 strain which is attenuated by a G to A substitution at nucleotide position 481 in a selected cell culture;

b. quantifying the percentage of revertant viruses having an A to G reversion at nucleotide position 481; and c. comparing the percentage of revertant viruses having the A to G reversion at nucleotide position 481 to the percentage of revertant viruses having the A to G reversion at nucleotide position 481 in an accepted reference poliovirus strain which can pass the monkey neurovirulence test utilized by the World Health Organization, the presence of a greater percentage of reversions at nucleotide position 481 in the poliovirus strain cultured in the selected cell culture than in the reference poliovirus strain indicating a cell culture unsuitable for poliovirus type 2 vaccine production.

5. A method for determining the suitability of an attenuated poliovirus type 2 strain or seed poliovirus type 2 lot which is attenuated by a G to A substitution at nucleotide position 481 for vaccine production, comprising the steps of:

a. culturing the attenuated live poliovirus type 2 strain or seed poliovirus type 2 lot in a selected cell culture;

b. quantifying the percentage of revertant viruses having an A to G reversion at nucleotide position 481;

c. comparing the percentage of revertant viruses having an A to G reversion at nucleotide position 481 to the percentage of revertant viruses having an A to G reversion at nucleotide position 481 in an accepted reference poliovirus strain which can pass the monkey neurovirulence test utilized by the World Health Organization, the presence of a greater percentage of reversions at nucleotide position 481 in the poliovirus strain or seed poliovirus lot cultured in the selected cell culture than in the accepted reference poliovirus strain indicating poliovirus type 2 strain or seed poliovirus type 2 lot unsuitable for poliovirus vaccine production.

6. A kit for classifying a poliovirus type 2 vaccine which is attenuated by a G to A substitution at nucleotide position 481 as having either an acceptable or unacceptable level of neurovirulence, comprising:

a. a first and second oligonucleotide which selectively binds to the poliovirus type 2 RNA or corresponding DNA so as to detectably amplify by polymerase chain reaction the region containing position 481 of the viral genome; and b. a reagent for quantification of an A to G reversion at position 481 in the amplified region, wherein each oligonucleotide and the reagent are contained in separate containers.

7. A kit for classifying a poliovirus type 1 which is attenuated by an A to G substitution at nucleotide position 480 and a C to U substitution at nucleotide position 525 vaccine as having an unacceptable level of neurovirulence, comprising:

a. a first and second oligonucleotide which selectively binds to the poliovirus type 1 RNA or corresponding DNA so as to detectably amplify by polymerase chain reaction the region containing position 480 of the viral genome; and b. a reagent for quantification of a G to A reversion at position 480 in the amplified region, wherein each oligonucleotide and the reagent are contained in separate containers.

8. A kit for classifying a poliovirus type 1 vaccine which is attenuated by an A to G substitution at nucleotide position 480 and a C to U substitution at nucleotide position 525 as having an unacceptable level of neurovirulence, comprising:

a. a first and second oligonucleotide which selectively binds to the poliovirus type 1 RNA or corresponding DNA so as to detectably amplify by polymerase chain reaction the region containing position 525 of the vital genome; and b. a reagent for quantification of a U to C reversion at position 525 in the amplified region, wherein each oligonucleotide and the reagent are contained in separate containers.

9. A method of classifying an unclassified live poliovirus type 1 vaccine which is attenuated by an A to G substitution at nucleotide position 480 and a C to U substitution at nucleotide position 525 as having an acceptable or unacceptable level of neurovirulence, comprising, prior to vaccine administration, the steps of:

a) selectively amplifying a region of an unclassified poliovirus type 1 vaccine genome containing nucleotide position 480 and a region containing nucleotide position 525 using selectively mismatched primers, whereby a restriction endonuclease site which includes nucleotide position 480 and a restriction endonuclease site which includes nucleotide position 525 are created by introducing a site-specific mutation into each amplified region;

b) digesting an amount of the amplified region with a restriction endonuclease that specifically cleaves the amplified sequences in revertant viruses which contain a G to A reversion at nucleotide position 480 and with a restriction endonuclease that specifically cleaves the amplified sequences in revertant viruses which contain a U to C reversion at nucleotide position 525;

c) digesting an amount of the amplified region with a restriction endonuclease that specifically cleaves the amplified sequences in nonrevertant viruses which contain a G at nucleotide position 480 and with a restriction endonuclease that specifically cleaves the amplified sequences in nonrevertant viruses which contain a U at nucleotide position 525;

d) quantifying the percentage of revertant viruses in the unclassified vaccine; and e) comparing the percentage of revertant viruses in the unclassified vaccine to the percentage of revertant viruses in an accepted reference vaccine which can pass the monkey neurovirulence test utilized by the World Health Organization, an unclassified vaccine with a higher percentage of nucleotide position 480 G to A revertant viruses than in the reference vaccine or a higher percentage of nucleotide position 525 U to C revertant viruses than in the reference vaccine being classified as unacceptable and an unclassified vaccine with an equal or lower percentage of nucleotide position 480 G to A revertant viruses than in the reference vaccine and a higher percentage of nucleotide position 525 U to C revertant viruses than in the reference vaccine being classified as acceptable.

10. A method of classifying an unclassified live poliovirus type 1 vaccine which is attenuated by an A to G substitution at nucleotide position 480 as having an unacceptable level of neurovirulence, comprising, prior to vaccine administration, the steps of:

a) selectively amplifying a region of an unclassified poliovirus type 1 vaccine genome containing nucleotide position 480 using selectively mismatched primers, whereby a restriction endonuclease site which includes nucleotide position 480 in the selectively amplified region is created by introducing a site-specific mutation into the amplified region;

b) digesting an amount of the amplified region with a restriction endonuclease that specifically cleaves the amplified sequences in revertant viruses which contain a G to A reversion at nucleotide position 480;

c) digesting an amount of the amplified region with a restriction endonuclease that specifically cleaves the amplified sequences in nonrevertant viruses which contain a G at nucleotide position 480;

d) quantifying the percentage of revertant viruses in the unclassified vaccine; and e) comparing the percentage of revertant viruses in the unclassified vaccine to the percentage of revenant viruses in an accepted reference vaccine which can pass the monkey neurovirulence test utilized by the World Health Organization, an unclassified vaccine with a higher percentage of G to A revertant viruses than in the reference vaccine being classified as unacceptable.

11. A method of classifying an unclassified live poliovirus type 1 vaccine which is attenuated by a C to U substitution at nucleotide position 525 as having an unacceptable level of neurovirulence, comprising, prior to vaccine administration, the steps of:

a) selectively amplifying a region of an unclassified poliovirus type 1 vaccine genome containing nucleotide position 525 using selectively mismatched primers, whereby a restriction endonuclease site which includes nucleotide position 525 in the selectively amplified region is created by introducing a site-specific mutation into the amplified region;

b) digesting an amount of the amplified region with a restriction endonuclease that specifically cleaves the amplified sequences in revertant viruses which contain a U to C reversion at nucleotide position 525;

c) digesting an amount of the amplified region with a restriction endonuclease that specifically cleaves the amplified sequences in nonrevertant viruses which contain a U at nucleotide position 525;

d) quantifying the percentage of revertant viruses in the unclassified vaccine; and e) comparing the percentage of revertant viruses in the unclassified vaccine to the percentage of revertant viruses in an accepted reference vaccine which can pass the monkey neurovirulence test utilized by the World Health Organization, an unclassified vaccine with a higher percentage of U to C revertant viruses than in the reference vaccine being classified as unacceptable.

12. A method for classifying an unclassified live poliovirus type 1 vaccine which is attenuated by an A to G substitution at nucleotide position 480 and a C to U substitution at nucleotide position 525 as having an acceptable or unacceptable level of neurovirulence, comprising the steps of:

a. quantifying the percentage of revertant viruses contained in the unclassified vaccine prior to administration by testing for the presence of a G to A reversion at nucleotide position 480 and for the presence of a U to C reversion at nucleotide position 525; and b. comparing the percentage of revertant viruses in the unclassified vaccine to the percentage of revertant viruses in an accepted reference vaccine which can pass the monkey neurovirulence test utilized by the World Health Organization, an unclassified vaccine having a higher percentage of the G to A reversion at nucleotide position 480 or the U to C reversion at nucleotide position 525 than in the reference vaccine being classified as unacceptable and an unclassified vaccine having an equal or lower percentage of both the G to A reversion at nucleotide position 480 and the U to C reversion at nucleotide position 525 than in the reference vaccine being classified as acceptable.

13. A method for classifying an unclassified live poliovirus type 1 vaccine which is attenuated by an A to G substitution at nucleotide position 480 and a C to U substitution at nucleotide position 525 as having an unacceptable level of neurovirulence, comprising the steps of:

a. quantifying the percentage of revertant viruses contained in the unclassified vaccine prior to administration by testing for the presence of a G to A reversion at nucleotide position 480; and b. comparing the percentage of revertant viruses in the unclassified vaccine to the percentage of revertant viruses in an accepted reference vaccine which can pass the monkey neurovirulence test utilized by the World Health Organization, an unclassified vaccine having a higher percentage of the G to A reversion at nucleotide position 480 than in the reference vaccine being classified as unacceptable.

14. A method for classifying an unclassified live poliovirus type 1 vaccine which is attenuated by an A to G substitution at nucleotide position 480 and a C to U substitution at nucleotide position 525 as having an unacceptable level of neurovirulence, comprising the steps of:

a. quantifying the percentage of revertant viruses contained in the unclassified vaccine prior to administration by testing for the presence of a U to C reversion at nucleotide position 525; and b. comparing the percentage of revertant viruses in the unclassified vaccine to the percentage of revertant viruses in an accepted reference vaccine which can pass the monkey neurovirulence test utilized by the World Health Organization, an unclassified vaccine having a higher percentage of the U to C reversion at nucleotide position 525 than in the reference vaccine being classified as unacceptable.

15. A method for determining the suitability of a cell culture for production of a poliovirus type 1 vaccine which is attenuated by an A to G substitution at nucleotide position 480 and a C to U substitution at nucleotide position 525, comprising the steps of:

a. culturing an attenuated live poliovirus type 1 strain which is attenuated by an A to G substitution at nucleotide position 480 and a C to U substitution at nucleotide position 525 in a selected cell culture;

b. quantifying the percentage of revertant viruses having a G to A reversion at nucleotide position 480 or a U to C reversion at nucleotide position 525; and c. comparing the percentage of revertant viruses having the G to A reversion at nucleotide position 480 or the U to C reversion at nucleotide position 525 to the percentage of revertant viruses having the G to A reversion at nucleotide position 480 or the U to C reversion at nucleotide position 525 in an accepted reference poliovirus strain which can pass the monkey neurovirulence test utilized by the World Health Organization, the presence of a greater percentage of reversions at either nucleotide position 480 or nucleotide position 525 in the poliovirus strain cultured in the selected cell culture than in the reference poliovirus strain indicating a cell culture unsuitable for poliovirus type 1 vaccine production.

16. A method for determining the suitability of an attenuated poliovirus type 1 strain or seed poliovirus type 1 lot which is attenuated by an A to G substitution at nucleotide position 480 and a C to U substitution at nucleotide position 525 for vaccine production, comprising the steps of:

a. culturing the attenuated live poliovirus type 1 strain or seed poliovirus type 1 lot in a selected cell culture;

b. quantifying the percentage of revertant viruses having a G to A reversion at nucleotide position 480 or a U to C reversion at nucleotide position 525;

c. comparing the percentage of revertant viruses having a G to A reversion at nucleotide position 480 or a U to C reversion at nucleotide position 525 to the percentage of revertant viruses having a G to A reversion at nucleotide position 480 or a C to U reversion at nucleotide position 525 in an accepted reference poliovirus strain which is attenuated by an A to G substitution at nucleotide position 480 and a C to U substitution at nucleotide position 525 and which can pass the monkey neurovirulence test utilized by the World Health Organization, the presence of a greater percentage of reversions at nucleotide position 480 or 525 in the poliovirus strain or seed poliovirus lot cultured in the selected cell culture than in the accepted reference poliovirus strain indicating poliovirus type 1 strain or seed poliovirus type 1 lot unsuitable for poliovirus vaccine production.

17. A kit for classifying a poliovirus type 1 vaccine which is attenuated by an A to G substitution at nucleotide position 480 and a C to U substitution at nucleotide position 525 as having either an acceptable or unacceptable level of neurovirulence, comprising:

a. a first and second oligonucleotide which selectively binds to the poliovirus type 1 RNA or corresponding DNA so as to detectably amplify by polymerase chain reaction the region containing position 480 of the viral genome;

b. a first and second oligonucleotide which selectively binds to the poliovirus type 1 RNA or corresponding DNA so as to detectably amplify by polymerase chain reaction the region containing position 525 of the viral genome;

c. a reagent for quantification of a G to A reversion at position 480 in the amplified region; and d. a reagent for quantification of a U to C reversion at position 525 in the amplified region, wherein each oligonucleotide and each reagent are contained in separate containers.

* * * * *

SEQUENCE LISTING ( 1 ) GENERAL INFORMATION:

( i i i ) NUMBER OF SEQUENCES: 77

( 2 ) INFORMATION FOR SEQ ID NO:1:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:1:

```
AGCTGATCGA TGGGCTACCA TGCGTACCCT AGCTGTTAAA ACAGCTCTGG GGTTGGACTC    60
ACCCCAGAGG AAA                                                      73
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:2:

```
AGCTGATCGA TGGGCTACCA TGCGTACCCT                                    30
```

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:3:

```
GGCTTCTCGA AGTACATAAG CGGATAACGG ATC                                33
```

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:4:

```
GGGAGTATAA AACAGGCGTA CAAGGGTACC                                    30
```

( 2 ) INFORMATION FOR SEQ ID NO:5:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:5:

AGCTGATCGA TGGGCTACCA TGCGTACCCT TTTTTTTTTT TTTTTTTT    49

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:6:

GCTCCCAGAG TACTCAACAT TGTACCGCCG TTG    33

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:7:

AGCTGATCGA TGGGCTACCA TGCGTACCCT    30

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:8:

GACTCATTTT AGTAACCCTA CCTCAGTCGA ATTGG    35

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:9:

AGCCTATTGG GCTACATAAG AATCCTCCGG CCC    33

( 2 ) INFORMATION FOR SEQ ID NO:10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:10:

CGACAGGCCA ATCACTGGTT TGTGACCACC AG    32

( 2 ) INFORMATION FOR SEQ ID NO:11:

( i ) SEQUENCE CHARACTERISTICS:
       ( A ) LENGTH: 32 base pairs
       ( B ) TYPE: nucleic acid
       ( C ) STRANDEDNESS: single
       ( D ) TOPOLOGY: linear ( i i ) MOLECULE TYPE: Other nucleic acid ( x i ) SEQUENCE DESCRIPTION: SEQ ID NO:11:

GTGGTCACAA ACCAGTGATT GGCCTGTCGT AA                              3 2

( 2 ) INFORMATION FOR SEQ ID NO:12:

( i ) SEQUENCE CHARACTERISTICS:
       ( A ) LENGTH: 34 base pairs
       ( B ) TYPE: nucleic acid
       ( C ) STRANDEDNESS: single
       ( D ) TOPOLOGY: linear ( i i ) MOLECULE TYPE: Other nucleic acid ( x i ) SEQUENCE DESCRIPTION: SEQ ID NO:12:

AACACGGACA CCCAAAGTAG TCGGTTCCGC TCCG                            3 4

( 2 ) INFORMATION FOR SEQ ID NO:13:

( i ) SEQUENCE CHARACTERISTICS:
       ( A ) LENGTH: 34 base pairs
       ( B ) TYPE: nucleic acid
       ( C ) STRANDEDNESS: single
       ( D ) TOPOLOGY: linear ( i i ) MOLECULE TYPE: Other nucleic acid ( x i ) SEQUENCE DESCRIPTION: SEQ ID NO:13:

GGCTGCTTAT GGTGACAATC ACAGATTGTG AGCA                            3 4

( 2 ) INFORMATION FOR SEQ ID NO:14:

( i ) SEQUENCE CHARACTERISTICS:
       ( A ) LENGTH: 35 base pairs
       ( B ) TYPE: nucleic acid
       ( C ) STRANDEDNESS: single
       ( D ) TOPOLOGY: linear ( i i ) MOLECULE TYPE: Other nucleic acid ( x i ) SEQUENCE DESCRIPTION: SEQ ID NO:14:

GATAATGAAT CTCACTTTCA CCGGATGGCC AATCC                           3 5

( 2 ) INFORMATION FOR SEQ ID NO:15:

( i ) SEQUENCE CHARACTERISTICS:
       ( A ) LENGTH: 32 base pairs
       ( B ) TYPE: nucleic acid
       ( C ) STRANDEDNESS: single
       ( D ) TOPOLOGY: linear ( i i ) MOLECULE TYPE: Other nucleic acid ( x i ) SEQUENCE DESCRIPTION: SEQ ID NO:15:

CAGCGAAGCC AATCCAGTGG ACCAGCCGAC AG                              3 2

( 2 ) INFORMATION FOR SEQ ID NO:16:

( i ) SEQUENCE CHARACTERISTICS:
       ( A ) LENGTH: 35 base pairs
       ( B ) TYPE: nucleic acid (C) STRANDEDNESS: single
(D) TOPOLOGY: linear (ii) MOLECULE TYPE: Other nucleic acid (xi) SEQUENCE DESCRIPTION: SEQ ID NO:16:

GACACGGTGT CTAGCGTATA AAACCTGCAT GCACC     35

(2) INFORMATION FOR SEQ ID NO:17:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: Other nucleic acid (xi) SEQUENCE DESCRIPTION: SEQ ID NO:17:

GCCGACAGAA CCAGACGTCG CTGCATGCAG GTTGT     35

(2) INFORMATION FOR SEQ ID NO:18:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: Other nucleic acid (xi) SEQUENCE DESCRIPTION: SEQ ID NO:18:

CACCACCCTC GCGACTCTTT CGTCCAAGAC ACGGT     35

(2) INFORMATION FOR SEQ ID NO:19:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: Other nucleic acid (xi) SEQUENCE DESCRIPTION: SEQ ID NO:19:

TATCAAAATG CCAATCCTGG CGAGAAAGGA GGCAC     35

(2) INFORMATION FOR SEQ ID NO:20:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: Other nucleic acid (xi) SEQUENCE DESCRIPTION: SEQ ID NO:20:

TAATCCACCG GGCAGAACCT ACGGCCAGGT GATGT     35

(2) INFORMATION FOR SEQ ID NO:21:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Other nucleic acid ( x i ) SEQUENCE DESCRIPTION: SEQ ID NO:21:

GTCAGCGTGT AATGACTTCA GCGTGCGCTT                                30

( 2 ) INFORMATION FOR SEQ ID NO:22:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:22:

AACCCCTGTG CTAGCGCTTT TTGCTCTATA TGTG                           34

( 2 ) INFORMATION FOR SEQ ID NO:23:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:23:

GTCTAGCATA GAGTCTTTCT TCGCGCGGGG TGCATACGT                      39

( 2 ) INFORMATION FOR SEQ ID NO:24:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:24:

CTTATTCTTG GTGGAAGCTG AGTTATCCAC GG                             32

( 2 ) INFORMATION FOR SEQ ID NO:25:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:25:

CTCAGCTTCA CCAAGAATAA GGATAAGCTA TCT                            33

( 2 ) INFORMATION FOR SEQ ID NO:26:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:26:

TCCTCCGTAA CTGGACAGTA TCTTTATAAG TG                             32

( 2 ) INFORMATION FOR SEQ ID NO:27:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:27:

TCCCATGGCT ACTGAAATGT GTAAGAACTG TGATC                      35

( 2 ) INFORMATION FOR SEQ ID NO:28:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:28:

GTCCATTAAT TGAATTGCCT TACCACACAC TAAAG                      35

( 2 ) INFORMATION FOR SEQ ID NO:29:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:29:

TCCCATGGCT ACTGAAATGT GTAAGAACTG TGATC                      35

( 2 ) INFORMATION FOR SEQ ID NO:30:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:30:

GTCCATTAAT TGAATTGCCT TACCACACAC TAAAG                      35

( 2 ) INFORMATION FOR SEQ ID NO:31:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:31:

TGGGTCATAC TGCTGTAGGG GTAAATTTTT CTTTAATTCG GTG              43

( 2 ) INFORMATION FOR SEQ ID NO:32:

( i ) SEQUENCE CHARACTERISTICS:
        ( A ) LENGTH: 36 base pairs
        ( B ) TYPE: nucleic acid (C) STRANDEDNESS: single
(D) TOPOLOGY: linear (i i) MOLECULE TYPE: Other nucleic acid (x i) SEQUENCE DESCRIPTION: SEQ ID NO:32:

GCGTTGGCGG CCTACCTATG GCTAACGCCA TAGGAC    36

(2) INFORMATION FOR SEQ ID NO:33:

(i) SEQUENCE CHARACTERISTICS:
(A) LENGTH: 34 base pairs
(B) TYPE: nucleic acid
(C) STRANDEDNESS: single
(D) TOPOLOGY: linear (i i) MOLECULE TYPE: Other nucleic acid (x i) SEQUENCE DESCRIPTION: SEQ ID NO:33:

GCCTTGTCCG CCAGCGCTTG GTCACTGACC GAAC    34

(2) INFORMATION FOR SEQ ID NO:34:

(i) SEQUENCE CHARACTERISTICS:
(A) LENGTH: 35 base pairs
(B) TYPE: nucleic acid
(C) STRANDEDNESS: single
(D) TOPOLOGY: linear (i i) MOLECULE TYPE: Other nucleic acid (x i) SEQUENCE DESCRIPTION: SEQ ID NO:34:

CATTCCTCAC CGGTGACGGT GGTCCAGGCT GCGTT    35

(2) INFORMATION FOR SEQ ID NO:35:

(i) SEQUENCE CHARACTERISTICS:
(A) LENGTH: 35 base pairs
(B) TYPE: nucleic acid
(C) STRANDEDNESS: single
(D) TOPOLOGY: linear (i i) MOLECULE TYPE: Other nucleic acid (x i) SEQUENCE DESCRIPTION: SEQ ID NO:35:

TACTCAGGAG GCCGGGGACT TACGCCGATT AGGAT    35

(2) INFORMATION FOR SEQ ID NO:36:

(i) SEQUENCE CHARACTERISTICS:
(A) LENGTH: 35 base pairs
(B) TYPE: nucleic acid
(C) STRANDEDNESS: single
(D) TOPOLOGY: linear (i i) MOLECULE TYPE: Other nucleic acid (x i) SEQUENCE DESCRIPTION: SEQ ID NO:36:

GCTACATAAG AGTCCTCCGG CCCCTGAATG CGGCT    35

(2) INFORMATION FOR SEQ ID NO:37:

(i) SEQUENCE CHARACTERISTICS:
(A) LENGTH: 38 base pairs
(B) TYPE: nucleic acid
(C) STRANDEDNESS: single
(D) TOPOLOGY: linear (i i) MOLECULE TYPE: Other nucleic acid -continued ( x i ) SEQUENCE DESCRIPTION: SEQ ID NO:37:

TGCACCAGCG CTTGGTCACT GACCGAACAG CATTGCGC                                    3 8

( 2 ) INFORMATION FOR SEQ ID NO:38:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:38:

TGAATGCGGC TAATCCTAAC CACGGAACAG GTGAT                                       3 5

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:39:

CTTGGTCACT GACCGAACAG CATTGCGCGT                                             3 0

( 2 ) INFORMATION FOR SEQ ID NO:40:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:40:

GTCAGGTATA CAACTGTTTG TTGGAACCGA TGTGT                                       3 5

( 2 ) INFORMATION FOR SEQ ID NO:41:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:41:

GATGTTACCC GCGGGTTCAA AGTAGTGTCT TTC                                         3 3

( 2 ) INFORMATION FOR SEQ ID NO:42:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:42:

CTGTTTGTTG GAACCACTGT GTTAGCTTTA CTACAC                                      3 6

( 2 ) INFORMATION FOR SEQ ID NO:43:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:43:

ACATTGGTTA ATTAGTTTTT GTTATGCTCC TATTTTG     37

( 2 ) INFORMATION FOR SEQ ID NO:44:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:44:

CAATTACTAT AGGGACTCTG CAAGCAATGC A     31

( 2 ) INFORMATION FOR SEQ ID NO:45:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:45:

TGCGTTCGTT CTAAAACGTG TTCTAGGCAG G     31

( 2 ) INFORMATION FOR SEQ ID NO:46:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:46:

CAATTACTAT AGGGACTCTG CAAGCAATGC A     31

( 2 ) INFORMATION FOR SEQ ID NO:47:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:47:

TGCGTTCGTT CTAAAACGTG TTCTAGGCAG G     31

( 2 ) INFORMATION FOR SEQ ID NO:48:

( i ) SEQUENCE CHARACTERISTICS:
        ( A ) LENGTH: 35 base pairs
        ( B ) TYPE: nucleic acid ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:48:

CTTATTAAGA CCGCTCCCTT GCTAAACTCC CCACA    35

( 2 ) INFORMATION FOR SEQ ID NO:49:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:49:

ACCTCCGCAC ACCAATATCA CTGTCCCATT ACGTC    35

( 2 ) INFORMATION FOR SEQ ID NO:50:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:50:

AGGCAAATCC TGTAGACCAA CCAACCGAGC    30

( 2 ) INFORMATION FOR SEQ ID NO:51:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:51:

TCCATCGGCG CACGTCCAAG ATGTGTAATC TATGG    35

( 2 ) INFORMATION FOR SEQ ID NO:52:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:52:

ACAAGTCAAC GCAGAAACAC AATGGACATG    30

( 2 ) INFORMATION FOR SEQ ID NO:53:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:53:

TGTCAGCTCA GCTCGCTGTG CCGAGTGAGA CTGTG    35

( 2 ) INFORMATION FOR SEQ ID NO:54:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:54:

CAAACTGGAA TTTTTCACAT ATTCGAGATT    30

( 2 ) INFORMATION FOR SEQ ID NO:55:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:55:

GTACCTCCAG TGAAAACACC AGTGGAGTTT GATG    34

( 2 ) INFORMATION FOR SEQ ID NO:56:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:56:

GAGTTCACTT TTGTGGTCAC CTCAAACTAC    30

( 2 ) INFORMATION FOR SEQ ID NO:57:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:57:

ATTCCGTTTA TTGCCTGTAC GTAACTTGGT TCAAA    35

( 2 ) INFORMATION FOR SEQ ID NO:58:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:58:

GAGTTCACTT TTGTGGTCAC CTCAAACTAC    30

( 2 ) INFORMATION FOR SEQ ID NO:59:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:59:

ATTCCGTTTA TTGCCTGTAC GTAACTTGGT TCAAA                      35

( 2 ) INFORMATION FOR SEQ ID NO:60:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:60:

GTGTTGATTA TAAAGATGGG CTCACCCCAC TATTA                      35

( 2 ) INFORMATION FOR SEQ ID NO:61:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:61:

TCTCCCTAAA TGCTGAATAC CTAAACCTGT GGTTT                      35

( 2 ) INFORMATION FOR SEQ ID NO:62:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:62:

TGATTATAAA GATGGGCTCA CCCCACTACC TGAAG                      35

( 2 ) INFORMATION FOR SEQ ID NO:63:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:63:

AATTGCTGAA TACCTAAACC TGTGGTTTTG                              30

( 2 ) INFORMATION FOR SEQ ID NO:64:

( i ) SEQUENCE CHARACTERISTICS:
        ( A ) LENGTH: 35 base pairs
        ( B ) TYPE: nucleic acid (C) STRANDEDNESS: single
(D) TOPOLOGY: linear (i i) MOLECULE TYPE: Other nucleic acid (x i) SEQUENCE DESCRIPTION: SEQ ID NO:64:

GTGATTGTGG TGGCATACTT AGATGTCAAC ACGCG     35

(2) INFORMATION FOR SEQ ID NO:65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: Other nucleic acid (x i) SEQUENCE DESCRIPTION: SEQ ID NO:65:

TATCCTTATT AGTGACGACC ACCCCTTCCG     30

(2) INFORMATION FOR SEQ ID NO:66:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: Other nucleic acid (x i) SEQUENCE DESCRIPTION: SEQ ID NO:66:

ACACGGGGTG ATAGGAATAA TCACTGCTGG TGG     33

(2) INFORMATION FOR SEQ ID NO:67:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: Other nucleic acid (x i) SEQUENCE DESCRIPTION: SEQ ID NO:67:

TCTGAAGCAA CGTAAAAGTC TGTAATCTCT GGACA     35

(2) INFORMATION FOR SEQ ID NO:68:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: Other nucleic acid (x i) SEQUENCE DESCRIPTION: SEQ ID NO:68:

GGTGCTGCAT TTGGTAGTGG ATTCACTCAA CAACT     35

(2) INFORMATION FOR SEQ ID NO:69:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: Other nucleic acid ( x i ) SEQUENCE DESCRIPTION: SEQ ID NO:69:

ACTATTTCAA AGGCTCGATT GGTCGTACCA T                    31

( 2 ) INFORMATION FOR SEQ ID NO:70:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:70:

CCTTGGGTGC GACATCTCAC CGTGGCAGTG GCTTA                 35

( 2 ) INFORMATION FOR SEQ ID NO:71:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:71:

TGACGCCGTA CATTACGACG TTTCCCTGAC CTCA                  34

( 2 ) INFORMATION FOR SEQ ID NO:72:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:72:

TACACCAATC TTGTCCAAGT CAAGAACATC AGTAG                 35

( 2 ) INFORMATION FOR SEQ ID NO:73:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:73:

AATAAGTTGT TACACGCCAC CGATAGATAG                       30

( 2 ) INFORMATION FOR SEQ ID NO:74:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:74:

CTAAAAGGAT TCAAAGCTG GAGCATACCA TAATTA                 36

(2) INFORMATION FOR SEQ ID NO:75:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:75:

TACATGTCAA GTTCTCGTTC GTGGCATAAC TCGGT      35

(2) INFORMATION FOR SEQ ID NO:76:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:76:

ATGGCAATGG CTACTGAAAT GTGCAAAAAC TGTGAT      36

(2) INFORMATION FOR SEQ ID NO:77:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:77:

GTCGTTTGAA GTTTTCTACA ACAGGAAATC      30